United States Patent
Kumar et al.

(10) Patent No.: US 12,024,733 B2
(45) Date of Patent: Jul. 2, 2024

(54) BIO-ASSISTED PROCESS FOR CONVERSION OF CARBON DIOXIDE TO FUEL PRECURSORS

(71) Applicant: INDIAN OIL CORPORATION LIMITED, Maharashtra (IN)

(72) Inventors: Manoj Kumar, Faridabad (IN); Prakash Chandra Sahoo, Faridabad (IN); Srikanth Sandipam, Faridabad (IN); Suresh Kumar Puri, Faridabad (IN); Sankara Sri Venkata Ramakumar, Faridabad (IN)

(73) Assignee: INDIAN OIL CORPORATION LIMITED, Mumbai (IN)

(*) Notice: Subject to any disclaimer, the term of this patent is extended or adjusted under 35 U.S.C. 154(b) by 1310 days.

(21) Appl. No.: 16/296,172

(22) Filed: Mar. 7, 2019

(65) Prior Publication Data

US 2019/0292571 A1    Sep. 26, 2019

(30) Foreign Application Priority Data

Mar. 8, 2018    (IN) .............................. 201821008490

(51) Int. Cl.
*C12P 7/54*    (2006.01)
*B01J 27/04*   (2006.01)
*C12N 1/20*    (2006.01)
*C12P 7/04*    (2006.01)
*C12P 7/06*    (2006.01)
(Continued)

(52) U.S. Cl.
CPC ................. *C12P 7/54* (2013.01); *B01J 27/04* (2013.01); *C12N 1/20* (2013.01); *C12P 7/04* (2013.01); *C12P 7/06* (2013.01); *C12P 7/065* (2013.01); *C12P 7/16* (2013.01); *C12P 7/40* (2013.01); *C12P 7/52* (2013.01); *C25B 3/25* (2021.01); *C25B 11/091* (2021.01); *C12N 2529/10* (2013.01)

(58) Field of Classification Search
CPC .... C12P 7/54; C12P 7/04; C12P 7/065; C12P 7/16; C12P 7/40; C12N 1/20; C12N 1/205; C12N 2529/10
See application file for complete search history.

(56) References Cited

U.S. PATENT DOCUMENTS 8,658,016 B2   2/2014   Lakkaraju et al.
9,175,408 B2   11/2015  Lovley et al.
(Continued)

FOREIGN PATENT DOCUMENTS

JP   2002-520032 A    7/2002
WO   2017/019146 A1   2/2017

OTHER PUBLICATIONS

Supplemental Materials of Sakimoto et al. (Science, 2016, 351(6268): 74-77) (Year: 2016).*

(Continued)

*Primary Examiner* — Allison M Fox
*Assistant Examiner* — Qing Xu
(74) *Attorney, Agent, or Firm* — Maschoff Brennan

(57) ABSTRACT

The present specification provides a semi-conducting biogenic hybrid catalyst capable of reducing $CO_2$ into fuel precursors. Specifically, the present application involves a method for bio-assisted conversion of $CO_2$ to fuel precursors using the semiconducting biogenic hybrid catalyst in a batch and a continuous mode.

11 Claims, 7 Drawing Sheets

(1) CO2 gas, (2) Gas Flow controller, (3) CO2 hydration in nutrient media (R2), (4) Bioreactor containing free microbial cells (R3), (5) H2S gas, (6) Semiconducting salt solution, (7) Cell separator, (8) Agitator, (9) Light source, (10) Biocatalyst/Cell (11) Cell separator (12) product separation by distillation or membrane separation or solvent extraction, (13) Purified product, (14) re-circulated liquid, (15) Cell recycling.

(51) Int. Cl.
*C12P 7/16* (2006.01)
*C12P 7/40* (2006.01)
*C12P 7/52* (2006.01)
*C25B 3/25* (2021.01)
*C25B 11/091* (2021.01)

(56) References Cited

U.S. PATENT DOCUMENTS

| | | | |
|---|---|---|---|
| 2006/0063043 | A1 | 3/2006 | Zeikus et al. |
| 2010/0120104 | A1 | 5/2010 | Reed |
| 2012/0288898 | A1 | 11/2012 | Lovley et al. |
| 2013/0008800 | A1 | 1/2013 | Lakkaraju et al. |
| 2015/0017694 | A1 | 1/2015 | Kurek et al. |
| 2017/0058409 | A1* | 3/2017 | Kumar ............ C25B 9/23 |
| 2017/0335473 | A1 | 11/2017 | Armiger et al. |
| 2018/0037914 | A1 | 2/2018 | Dodds et al. |
| 2018/0179512 | A1 | 6/2018 | Sakimoto et al. |
| 2018/0230028 | A1 | 8/2018 | Li |

OTHER PUBLICATIONS

Printout of 2D material—Wikipedia, downloaded on Jul. 3, 2023 from website of https://en.wikipedia.org/wiki/Single-layer_materials ( Year: 2023).*

Jourdin, L., et al., "Bringing High-Rate, CO2-Based Microbial Electrosynthesis Closer to Practical Implementation through Improved Electrode Design and Operating Conditions," Environmental Science & Technology, vol. 50, Issue 4, pp. 1982-1989 (Jan. 26, 2016).

Liu, C., et al., "Nanowire-bacteria hybrids for unassisted solar carbon dioxide fixation to value-added chemicals," Nano Letters, vol. 15, Issue 5, pp. 3634-3639 (Apr. 7, 2015).

Nevin, P.K., et al., "Microbial Electrosynthesis: Feeding Microbes Electricity To Convert Carbon Dioxide and Water to Multicarbon Extracellular Organic Compounds," vol. 1, Issue 2, pp. 4 (May/Jun. 2010).

Reisner, E., et al., "Visible Light-Driven H2 Production by Hydrogenases Attached to Dye-Sensitized TiO2 Nanoparticles," Journal of the American Chemical Society, vol. 131, Issue 51, pp. 18457-18466 (2009).

Sakimoto, K.K., et al., "Cyborgian Material Design for Solar Fuel Production: The Emerging Photosynthetic Biohybrid Systems," Accounts of Chemical Research, vol. 50, Issue 3, pp. 476-481 (Mar. 21, 2017).

Sakimoto, K.K., et al., "Self-photosensitization of nonphotosynthetic bacteria for solar-to-chemical production," Science, vol. 351, Issue 6268, pp. 74-77 (Jan. 1, 2016).

Yang Xet al., Chemical Physical Letters, Chemistry of Materials, vol. 651, pp. 127-132, 2016.

* cited by examiner (1) CO2 gas, (2) Gas Flow controller, (3) CO2 hydration in nutrient media (R2), (4) Bioreactor containing free microbial cells (R3), (5) H2S gas, (6) Semiconducting salt solution, (7) Cell separator, (8) Agitator, (9) Light source, (10) Biocatalyst /Cell (11) Cell separator (12) product separation by distillation or membrane separation or solvent extraction, (13) Purified product, (14) re-circulated liquid, (15) Cell recycling.

(1) CO2 gas, (2) Gas Flow controller, (3) CO2 hydration in nutrient media (R1), (4) Bioreactor (R2), (5) Light source, (6) Bio-film, (7) Semiconducting salt, (8) H2S gas, (9) product separation by distillation or membrane separation or solvent extraction, (10) re-circulated liquid (11) Purified product.

BIO-ASSISTED PROCESS FOR CONVERSION OF CARBON DIOXIDE TO FUEL PRECURSORS

FIELD OF THE INVENTION

The present invention relates to a carbon dioxide reduction process mediated by semiconducting biogenic catalyst.

BACKGROUND OF THE INVENTION

Oil refineries and coal-fired power plants are the leading anthropogenic source of $CO_2$ emission and are responsible for releasing over 9 billion metric tons of $CO_2$/year worldwide. Sustainable conversion of $CO_2$ to fuels and other value added chemical are of great importance in the current energy scenario. Natural photosynthesis harvests 130 TW of solar energy and generates up to 115 billion metric tons of biomass per year from the reduction of $CO_2$. The huge potential of this process motivates researchers to develop bio-mimetic systems that can convert $CO_2$ to value-added chemicals by harvesting solar energy.

Various processes for biocatalytic conversion of $CO_2$ to multi-carbon compounds have been disclosed in the prior art. Certain microbiological processes have been shown to interact electrochemically with electrodes that are capable of shuttling electrons between the electrodes and the microorganisms.

U.S. Pat. No. 9,175,408 B2 describes a process for the microbial production of multi carbon chemicals and fuels from water and carbon dioxide using electric current. The half reactions are driven by the application of electrical current from an external source. Compounds that have been produced include acetate, butanol, 2-oxobutyrate, propanol, ethanol, and formate. The patent discloses systems and methods for generating organic compounds using carbon dioxide as a source of carbon and electrical current as an energy source. A biological film on the cathode can accept electrons and that can convert carbon dioxide to a carbon-bearing compound and water in a cathode half-reaction. However, this process is quite expensive on an industrial scale, due to its complexity and high requirement of external electricity.

US 2015/0017694 A1 discloses several species of engineered $CO_2$-fixing chemotropic microorganisms producing carbon-based products. The invention shows that (a) Micro organisms are capable of growing on gaseous carbon dioxide, gaseous hydrogen, syngas, or combinations of all, (b) the microorganisms are chemotropic bacteria that produce 10% of lipid by weight, (c) also disclosed are methods of manufacturing chemicals or producing precursors to chemicals useful in jet fuel, diesel fuel, and biodiesel fuel. The chemicals obtained in such process includes alkanes, alkenes, alkynes, fatty acid alcohols, fatty acid aldehydes, desaturated hydrocarbons, unsaturated fatty acids, hydroxyl acids, or diacids with carbon chains between six and thirty carbon atoms long. The major disadvantage of this process is the requirement of $H_2$ gas and syngas (as it contains CO). Both of the gases are energy molecules, which makes their handling quite problematic in a large scale. Further, the process is energy intensive.

US 2010/0120104 A1 describes a process for the multi-step biological and chemical capture and conversion of carbon dioxide from inorganic carbon into organic chemicals including biofuels or other useful industrial, chemical, pharmaceutical, or biomass products. One or more process steps in the present invention utilize chemoautotrophic microorganisms to fix inorganic carbon into organic compounds through chemosynthesis. An additional feature of the present invention describes process steps whereby electron donors used for the chemosynthetic fixation of carbon are generated by chemical or electrochemical means, or are produced from inorganic or waste sources. The process reported is highly complex due to the involvement of multiple stages. Moreover, the multistage synchronization of chemical and biochemical process is expensive considering an industrial application.

U.S. Pat. No. 8,658,016 B2 describes a method for capture of carbon dioxide and electrochemical conversions of the captured carbon dioxide to organic products. A method may include, (a) the introduction of a solvent to a first compartment of an electrochemical cell where carbon dioxide is captured with guanidine, a guanidine derivative, pyrimidine, or a pyrimidine derivative to form carbamic zwitterions, (b) an electrical potential between an anode and a cathode sufficient for the cathode to reduce the carbamic zwitterions to a product mixture. The process needs external electrical bias to operate. This may be expensive considering the large scale application of the process. The material used in cathode and anode adds additional cost to the operational process.

US 2018/0179512 A1 describes a genetically modified non-photosynthetic microorganism, which comprises a bio-hybrid catalyst. The bio-hybrid catalyst consists of a semiconductor nanoparticle attached to the surface of the electro active microbe and is capable of photosynthesizing an organic compound from carbon dioxide using light. However, it does not disclose the use of any electron facilitating molecules in combination with the semiconducting material.

US 2018/0230028 A1 describes conversion of organic compounds in wastewater to chemical fuels. More specifically, the invention relates to solar-assisted microbial electrohydrogenesis by integrating two semiconductor photoelectrodes with a conventional microbial fuel cell (MFC) device.

Microbial electro-synthesis for conversion of $CO_2$ to chemical has been reported by various articles. For example, K. P. Nevin et al. MBio, 1(2), 103-110 (2010), Jourdin et al. *Environ. Sci. Technol.* 2016, 50 (4), pp 1982-1989, represents the enhancement of microbial electro-synthesis (MES) of acetate from $CO_2$ via an optimized design system. The authors have claimed that (a) higher proton availability drastically increases the acetate production rate, with pH 5.2 found to be optimal, which likely suppresses methanogenic activity without inhibitor addition, (b) applied cathode potential as low as −1.1 V versus SHE still achieved 99% of electron recovery in the form of acetate at a current density of around −200 $Am^{-2}$. These current densities lead to an acetate production rate of up to 1330 g $m^{-2}$ $day^{-1}$ at pH 6.7. (c) Using highly open macroporous reticulated vitreous carbon electrodes with macro-pore sizes of about 0.6 mm in diameter was found to be optimal for achieving a good balance between total surface area available for biofilm formation and effective mass transfer between the bulk liquid and the electrode and biofilm surface, (c) they demonstrated the use of a synthetic biogas mixture as carbon dioxide source, yielding similarly high MES performance as pure $CO_2$. In spite of several advantages, the process desires external electrical supply to operate. The overall process may be expensive considering an industrial scale application. The synthesis material used in cathode and anode is tedious and adds additional cost to the operational process.

Further, there are several limitations on the use of photosynthetic microbes for $CO_2$ capture. Intensity and wavelength of light affects productivity, requirement of a huge amount of water; requirement of large amounts of phosphorous as fertilizer, requirement of stringent pH and temperature conditions, nitrogen (e.g., nitrate, urea, and ammonia) is the most limiting nutrient for biomass production, agitation (e.g., aeration, pumping and mechanical stirring) is necessary, increasing the operating cost of cell cultivation. Therefore, genetic modification tools are highly essential to improve the productivity. Furthermore, a bioreactor or pond used to grow photosynthetic microbes such as algae must have a high surface area to volume ratio in order to allow each cell to receive enough light for carbon fixation and cell growth. Otherwise light blockage by cells on the surface will leave cells located towards the center of the volume in darkness turning them into net $CO_2$ emitters. This requirement of high surface area to volume ratio for efficient implementation of the algal and cyanobacterial technologies generally results in either a large land footprint (ponds) or high material costs (bioreactors). The types of materials that can be used in algal bioreactor construction are limited by the requirement that Walls lying between the light source and the algal growth environment need to be transparent. This requirement restricts the use of construction materials that would normally be preferred for use in large scale projects such as concrete, steel and earthworks. On the other hand, heterotrophic bacteria with acetyl coenzyme pathway are very fast growing and robust in nature. Their growth requirements are also very less stringent. Several researchers have shown that inorganic semiconducting nano particles when synthesized on the bacterium surface can improve their photo synthetic abilities. For instance, as a proof of principle, Liu et al. in the paper entitled "Nanowire bacteria hybrids for unassisted solar carbon dioxide fixation to value-added chemicals "*Nano Lett.*, 2015, 15, 3634-3639 demonstrate that (a) a hybrid semiconductor nanowire—bacteria system can reduce $CO_2$ at neutral pH to a wide array of chemical targets, such as fuels, polymers, and complex pharmaceutical precursors, using only solar energy input, (b) the high-surface-area silicon nanowire array harvests light energy to provide reducing equivalents to the anaerobic bacterium, *Sporomusa ovata*, for the photoelectrochemical production of acetic acid under aerobic conditions (21% 02) with low overpotential (η<200 mV), high Faradaic efficiency (up to 90%), and long-term stability (up to 200 h) (c) using genetically engineered *Escherichia coli* value-added chemicals such as n-butanol, polyhydroxybutyrate (PHB) polymer, and three different isoprenoid natural products can be obtained.

In another approach, Sakimoto et al. in the paper entitled "Self-photosensitization of nonphotosynthetic bacteria for solar-to-chemical production" *Science*, 351, 2016, 74-77 has demonstrated the combination of efficient light harvesting of inorganic semiconductors with the high specificity biocatalysts. The self-photosensitization of a non photosynthetic bacterium, *Moorella thermoacetica*, with cadmium sulfide nano-particles, results in photosynthesis of acetic acid from carbon dioxide. Cadmium sulfide nano-particles served as the light harvester to sustain cellular metabolism. The same group also designed a hybrid tandem inorganic-biological hybrid system capable of oxygenic photosynthesis of acetic acid from $CO_2$. The photo reductive catalyst consists of the bacterium *Moorella thermoacetica* self-photosensitized with CdS nanoparticles at the expense of the thiol amino acid cysteine (Cys) oxidation to the disulfide form cystine (CySS). To regenerate the CySS/Cys redox shuttle, the photooxidative catalyst, $TiO_2$ loaded with cocatalyst Mn(II) phthalocyanine (MnPc), couples water oxidation to CySS reduction. The combined system *M. thermoacetica*-CdS+ $TiO_2$—MnPc demonstrate a potential biomimetic approach to complete oxygenic solar-to-chemical production.

In yet another publication, Sakimoto et al. in the paper entitled "Cyborgian Material Design for Solar Fuel Production: The Emerging Photosynthetic Biohybrid Systems" *Acc. Chem. Res.*, 2017, 50 (3), pp 476-481 provides a study on photosynthetic biohybrid systems (PBSs) to combine the strengths of inorganic materials and biological catalysts by exploiting semiconductor broadband light absorption to capture solar energy and subsequently transform it into valuable $CO_2$-derived chemicals by taking advantage of the metabolic pathways in living organisms. The study disclosed that such systems have been demonstrated in the literature, offering several approaches to the PBS concept.

In a further publication, Reisner et al. in the paper entitled "Visible Light-Driven H2 Production by Hydrogenases Attached to Dye-Sensitized TiO2 Nanoparticles" *J. Am. Chem. Soc.*, 2009, 131 (51), pp 18457-18466 describes a study of hybrid, enzyme-modified nanoparticles able to produce H2 by water splitting using visible light as the energy source. Here, the [NiFeSe]-hydrogenase from electro active Desulfomicrobium baculatum is attached to Ru dye-sensitized TiO2 and used for the purpose described above.

One of the prominent drawbacks of the microbe semiconducting hybrid is that the extra cellular electrons from the semiconducting nano particle cannot effectively travel to the intracellular body via direct electron transfer. This obstructs the efficiency of the microbes in $CO_2$ to fuel conversion. In the process, no higher carbon compound of commercial value has been obtained. Moreover the process is not continuous. Further, $CO_2$ solubilization is a prominent issue during biological $CO_2$ conversion. In particular, it is apparent that most of the scientists consider MFC as the method for $CO_2$ conversion to different products. However, two major limitations associated with this process are (1) use of external electric stimuli for large scale application is cost intensive and (b) high cost of electrode and associated material.

Although, photosynthetic bacterium like genetically engineered cynobactor have been studied for $CO_2$ conversion; no wilder strain has been reported for such cases. The use of PEC based system using nano-wire bacteria system, however the process is tedious to scale up and electrode synthesis is quite const intensive. There have been reports on direct semiconducting material integrated microbes for $CO_2$ conversion. However, due to no effective contact between the bacterium surface and the light harvester, the facile electron transfer is prohibited resulting only in the production of acetate in low yield.

Accordingly, there is a need in the art for microbial method for continuous production of production of C1 and higher carbon compounds in a facile manner on a commercial scale. There is also a need for a standalone process that can be operated without many difficulties.

SUMMARY OF THE INVENTION

The present disclosure relates to a semi-conducting biogenic hybrid catalyst capable of reducing $CO_2$ into fuel precursors, said catalyst consisting:
  (a) electroactive microorganism selected from the group consisting of *Enterobacter aerogenes* MTCC 25016, *Serratia* sp. MTCC 25017, *Shewanella* sp. MTCC 25020, *Alcaligenes* sp. MTCC 25022, *Pseudomonas aeruginosa* MTCC 1036, *Ochrobactrum anthropi*

ATCC 49188, *Ochrobactrum anthropi* MTCC 9026, and *Pseudomonas alcaliphila* MTCC 6724; and
(b) semi conducting particles comprising a precursor metal component, electron facilitator and dye molecule;
wherein the semi conducting particles are located on cell surface of the electroactive microorganisms.

In accordance with an embodiment of the present disclosure, there is provided a process for synthesizing a semiconductor biogenic-hybrid catalyst, said process comprising:
(a) selectively culturing electroactive microorganisms selected from the group consisting of *Enterobacter aerogenes* MTCC 25016, *Serratia* sp. MTCC 25017, *Shewanella* sp. MTCC 25020, *Alcaligenes* sp. MTCC 25022, *Pseudomonas aeruginosa* MTCC 1036, *Ochrobactrum anthropi* ATCC 49188, *Ochrobactrum anthropi* MTCC 9026, and *Pseudomonas alcaliphila* MTCC 6724;
(b) mixing at least a salt, at least one 2D material, and an electron facilitator, in presence of a surface directing agent to obtain a semiconducting hybrid solution;
(c) adding the semiconducting hybrid solution of step (b) to the electroactive microorganism culture of step (a) to obtain an initiator culture;
(d) providing counter ion precursor to the initiator culture of step (c); and
(e) separating the semiconductor biogenic-hybrid catalyst from the culture;
wherein the salt is selected from the group consisting of $CuCl_2$, $CdCl_2$, $ZnCl_2$, $ZnBr_2$, $GaCl_3$, $InCl_3$, $FeCl_2$, $FeCl_3$, $SnCl_2$, $SnCl_4$, $Cd(NO_3)_2$, $Ga(NO_3)_3$, $Ln(NO_3)_3$, $Zn(NO_3)_2$, $Fe(NO_3)_3$, $CdCO_3$, $CdSO_4$, $FeSO_4$, $ZnSO_4$, $Fe_2O_3$, $CdO$, $Ga_2O_3$, $Ln_2O_3$, $ZnO$, $SnO$, $SnO_2$, $Fe(OH)_3$, $Zn(OH)_2$, $FeOOH$, $FeO(OH)$, $Cd(CH_3COO)_2$, Iron perchlorate, Copper perchlorate, Copper EDTA complex, Nickel alkylamine complex, Iron piperidine complex, Cadmium pyridine complex, Iron bipyridine salt and Iron acac complex;
wherein the 2D material is selected from the group consisting of graphene, porous graphene, $gC_3N_4$, single walled CNT, $MoS_2$, $WS_2$, $SnS_2$, phosphorene, graphene nanoparticles (Gr-Np), TiC, and borophene;
wherein the electron facilitator is selected from the group consisting of neutral red, azo-dyes, Iron porphyrin complex, Schiff base complex, multi walled CNT, Cd (II) or Cu (II) imidazole complex, and Ruthenium complex;
wherein the surface directing agent is selected from the group consisting of Tween, sodium lauryl sulfate, p-172, Lauryl dimethyl amine oxide, Cetyltrimethylammonium bromide, Polyethoxylated alcohol, Polyoxyethylene sorbitan Octoxynol (Triton X100), N, N-dimethyldodecylamine-N-oxide, Hexadecyltrimethylammonium bromide, Polyoxyl 10 lauryl ether, Brij 721, sodium deoxycholate, sodium cholate, Polyoxyl castor oil (Cremophor), Nonylphenol ethoxylate (Tergitol), Cyclodextrins, Lecithin, and Methylbenzethonium chloride (Hyamine); and
wherein the counter ion precursor is a gaseous material or an organosulfur compound.

BRIEF DESCRIPTION OF ACCOMPANYING DRAWINGS

DETAILED DESCRIPTION OF THE INVENTION

Figure 1:
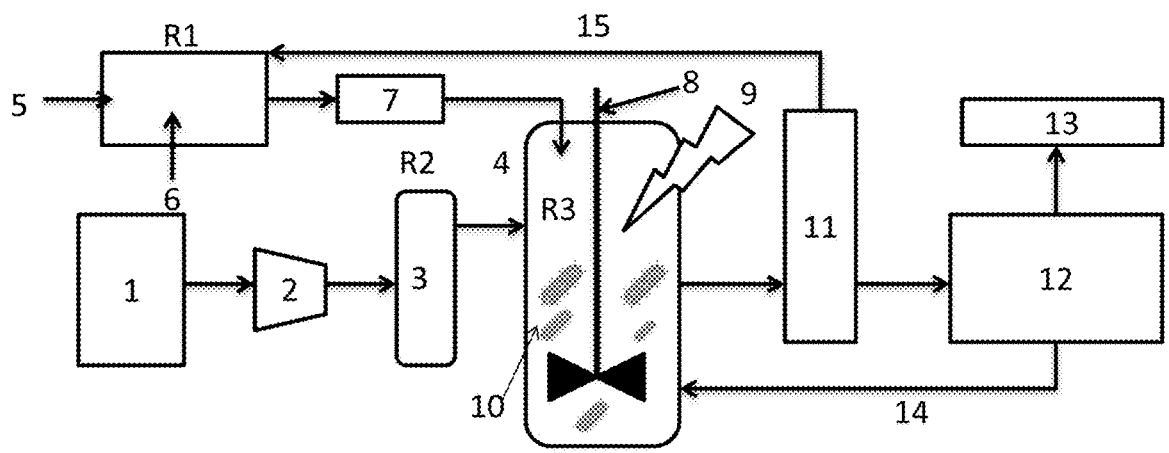
FIG. 1 depicts the schematic representation of continuous system for microbial $CO_2$ reduction in free cell condition.

The present invention discloses a light assisted method for conversion of $CO_2$ to fuel precursors using semiconducting biogenic hybrid catalyst. The present invention also discloses a method of synthesizing semiconducting particles on microbial cell surface in order to be used as a biogenic hybrid catalyst.

The process for generation of fuel precursors provided in the present application is simple and self-sustained. The semiconducting and biogenic hybrid catalyst of the invention is able to effectively convert $CO_2$ to chemicals in a one pot bioreactor. Notably, the process of the present invention does not require additional electricity from an external source, and the required electrons can be supplied to the microorganism of the biogenic hybrid catalyst by the attached semiconducting material on the cell surface. Further, a continuous process can be achieved by supplying semiconducting ions and $CO_2/H_2S$ gases.

Biogas results from anaerobic fermentation of organic waste. The raw biogas typically has a mixture of methane (70-80%) and carbon dioxide (20-30%) with hydrogen sulfide (0.005-3%), oxygen (0-1%), ammonia (<1%), trace amounts of siloxanes (0-0.02%), and moisture. To purify the biogas, the concentration of its major gaseous impurities such as $CO_2$ and $H_2S$ needs to be removed. As discussed above, the process disclosed in the present application involves the microbial utilization of both $CO_2$ as well as $H_2S$. Therefore, the present application is found to be highly useful for the biogas upgradation.

In accordance with the present invention, the semiconducting particle has been synthesized on the cell surface of the electroactive microbes according to the following steps:
a. selection of electroactive microbes having Acetyl-CoA pathway and growing the microbes in culture media;
b. in vitro preparation of semiconducting hybrid solution by using at least a salt and at least one 2D material and an electron facilitator in presence of a surface directing agent;
c. adding the semiconducting hybrid solution to the growing microbial culture;
d. development of semiconducting biogenic hybrid catalyst on the microbe surface by providing counter ions from $CO_2/H_2S$ gas or from any organic source;

e. separation of semiconducting biogenic hybrid catalyst and adding it to the culture media in a transparent reactor;

f. sparging $CO_2$ and providing light to the reactor at step 'e' during incubation at specified temperature and light intensity/duration;

g. separation of cells and obtaining broth with at least one multi carbon molecules from culture broth; and h. recycling of the cells.

The present invention further discloses the optimization of interfacial composition between semiconductors, 2D material and electron facilitator. The invention could offer a conceptually new strategy to boost the lifetime and transfer efficiency of photo-generated charge carriers across the interface between microbes. Consequently, there is an increase in electron density resulting in the formation of high molecular weight product. Further, controlled illumination of light (as utilized in the present invention) results in an increase in yield of the end product.

The genus of electro active microorganisms that can be used in one or more process steps of the present invention include but are not limited to one or more of the following: *Enterobacter aerogenes, Serratia* sp., *Alcaligenes* sp., *Ochrobactrum anthropi, Acidiphilium cryptum, Rhodopseudomonas palustris, Rhodoferax ferrireducens, Cupriavidus necator, Shewanella oneidensis, Shewanella putrefaciens, Pseudomonas aeruginosa, Pseudomonas alcaliphila, Pseudomonas fluorescens, Azotobacter vinelandii, Escherichia coli, Aeromonas hydrophila, Actinobacillus succinogenes, Klebsiella pneumonia, Klebsiella* sp. ME17, *Klebsiella terrigena, Enterobacter cloacae Citrobacter* sp. SX-1, *Geopsychrobacter, electrodiphilus, Geobacter sulfurreducens, Geobacter metallireducens, Geobacter lovleyi, Desulfuromonas acetoxidans, Desulfovibrio desulfuricans, Desulfovibrio paquesii, Desulfobulbus propionicus, Arcobacter butzleri, Acidithiobacillus ferrooxidans, Sporomusa ovate, Sporomusa sphaeroides, Sporomusa silvacetica, Thermincola* sp. JR, *Geothrix fermentans, Clostridium ljungdahlii, Clostridium aceticum, Clostridium* sp. EG3, *Moorella thermoacetica, Thermincola ferriacetica, Bacillus subtilis, Lactococcus lactis, Lactobacillus pentosus, Enterococcus faecium, Brevibacillus* sp. PTH1, *Corynebacterium glutamicum*.

In an embodiment of the present invention, the electro active microbes includes *Ochrobactrum anthropi* (ATCC 49188), (ATCC 29243), (ATCC 21909), (ATCC 49237), (ATCC 49187), DSM-14396, DSM-20150, MTCC-9026, MTCC-8748, *Acidiphilium cryptum* (ATCC 33463), DSM-2389, DSM-2390, DSM-2613 DSM-9467, *Rhodopseudomonas palustris* (ATCC 33872), (ATCC 17001), (ATCC 17010), (ATCC 17007) DSM-127 DSM-131 DSM-8283, *Rhodoferax ferrireducens* (ATCC BAA-621) DSM-15236(ATCC BAA-1852), *Cupriavidus necator* (ATCC 17697), (ATCC 43291) (ATCC 17699), MTCC-1472, DSM-11098 DSM-13439, DSM-15443, *Shewanella oneidensis* (ATCC 700550), (ATCC BAA-1096) (ATCC 700550D), *Shewanella putrefaciens* MTCC-8104, (ATCC 8071), (ATCC 8072), DSM-9439 DSM-1818 DSM-50426, *Pseudomonas aeruginosa*, (ATCC 10145), (ATCC 15442-MINI-PACK), (ATCC 9027-MINI-PACK) DSM-100465, DSM-102273 DSM-102275, MTCC-1036, MTCC-1688, *Pseudomonas alcahphila* MTCC-6724, DSM-17744, DSM-26533

In another embodiment of the present invention, the electro active microorganism is selected from the group selected from *Enterobacter aerogenes* MTCC 25016, *Serratia* sp. MTCC 25017, *Shewanella* sp. MTCC 25020, *Alcaligenes* sp. MTCC 25022, *Pseudomonas aeruginosa* MTCC 1036, *Ochrobactrum anthropi* ATCC 49188, *Ochrobactrum anthropi* MTCC 9026, and *Pseudomonas alcahphila* MTCC 6724.

In another aspect, the invention is directed to a semiconductor composition produced by bio-assisted method. In an embodiment, the semiconducting particles have a composition, such as CdS, ZnS, SnS, CdSe, ZnSe, CdTe, ZnTe, or CdS—ZnS. The precursor metal component contains one or more types of metals in ionic form. Some examples of precursor metal compounds applicable herein include the metal halides (e.g., $CuCl_2$, $CdCl_2$, $ZnCl_2$, $ZnBr_2$, $GaCl_3$, $InCl_3$, $FeCl_2$, $FeCl_3$, $SnCl_2$, and $SnCl_4$), metal nitrates (e.g., $Cd(NO_3)_2$, $Ga(NO_3)_3$, $In(NO_3)_3$, $Zn(NO_3)_2$, and $Fe(NO_3)_3$), metal perchlorates (Copper perchlorate), metal carbonates (e.g., $CdCO_3$), metal sulfates (e.g., $CdSO_4$, $FeSO_4$, and $ZnSO_4$), metal oxides (e.g., $Fe_2O_3$, CdO, $Ga_2O_3$, $Ln_2O_3$, ZnO, SnO, $SnO_2$), metal hydroxides (e.g., $Fe(OH)_3$ and $Zn(OH)_2$), metal oxyhydroxides (e.g., FeOOH, or FeO(OH), and their alternate forms), Iron and Copper EDTA complexes, metal amines (e.g., metal alkylamine, piperidine, pyridine, or bipyridine salt complexes of Iron, Zinc and Nickel), metal carboxylates (e.g., cadmium acetate), and metal acetylacetonate (i.e., metalacac) complexes of Iron, Copper, Cadmium and Nickel.

In another embodiment of the present invention, the 2D material is selected from the group consisting of graphene, porous graphene, graphene nanoparticles, $gC_3N_4$, single walled CNT, $MoS_2$, TiC, $WS_2$, $SnS_2$, phosphorene, and borophene.

In a further embodiment of the present invention, the electron facilitators are selected from the group consisting of neutral red, azo-dye, porphyrin complex, Schiff base complex, multi walled CNT, Cd (II) imidazole complex, Cu (II) imidazole complex, and Ruthenium complex.

Yet another embodiment of the present invention provides that the surface directing agents are selected from the group consisting of Polysorbate (Tween), Sodium dodecyl sulfate (sodium lauryl sulfate), Lauryl dimethyl amine oxide, Cetyltrimethylammonium bromide (CTAB), Polyethoxylated alcohol, Polyoxyethylene sorbitan Octoxynol (Triton X100), N,N-dimethyldodecyl amine-N-oxide, Hexadecyltrimethylammonium bromide (HTAB), Polyoxyl 10 lauryl ether, Brij 721, sodium deoxycholate, sodium cholate, Polyoxyl castor oil (Cremophor), Nonylphenol ethoxylate (Tergitol), Cyclodextrins, Lecithin, and Methylbenzethonium chloride (Hyamine).

In still another embodiment of the present invention, there is provided that the counter ion precursors are gaseous sources selected from the group consisting of $H_2S$ containing gas, Industrial flue gas, bio gas. In another embodiment, the counter ion precursors are suitable organosulfur compounds including the hydrocarbon mercaptans (e.g., methanethiol, ethanethiol, propanethiol, butanethiol, thiophenol, ethanedithiol, 1,3propanedithiol, 1,4 butanedithiol, thiophene), the alcohol containing mercaptans (e.g., 2mercaptoethanol, 3 mercaptopropanol, 4-mercaptophenol, and dithiothreitol), the mercapto amino acids (e.g., cysteine, homocysteine, methionine, thioserine, thiothreonine, and thiotyrosine), mercapto peptides (e.g., glutathione), the mercaptopyrimidines (e.g., 2thiouracil, 6methyl2 thiouracil, 4thiouracil, 2,4dithiouracil, 2-thiocytosine, 5-methyl-2-thiocytosine, 5-fluoro-2-thiocytosine, 2-thiothymine, 4thiothymine, 2,4-dithiothymine, and their nucleoside and nucleotide analogs), the mercapto purines (e.g., 6-thioguanine, 8-thioadenine, 2-thioxanthine, 6-thioxanthine, 6-thiohypoxanthine, 6-thiopurine, and their nucleoside and nucleotide analogs), the thioethers (e.g., dimethylsulfide, diethylsulfide, diphenylsulfide, biotin), the disulfides (e.g., cystine, lipoic acid, diphenyl disulfide, iron disulfide, and 2 hydroxyethyl-disulfide), the thiocarboxylic acids (e.g., thioacetic acid), the thioesters, the sulfonium salts (e.g., trimethylsulfonium or diphenylmethylsulfonium chloride), the sulfoxides (e.g., dimethylsulfoxide), the sulfones (e.g., dimethylsulfone), thioketones, thioamides, thiocyanates, isothiocyanates, thiocarbamates, dithiocarbamates.

An embodiment of the present invention provides a semi-conducting biogenic hybrid catalyst capable of reducing $CO_2$ into fuel precursors, said catalyst consisting:
(c) electroactive microorganism selected from the group consisting of *Enterobacter aerogenes* MTCC 25016, *Serratia* sp. MTCC 25017, *Shewanella* sp. MTCC 25020, *Alcaligenes* sp. MTCC 25022, *Pseudomonas aeruginosa* MTCC 1036, *Ochrobactrum anthropi* ATCC 49188, *Ochrobactrum anthropi* MTCC 9026, and *Pseudomonas alcaliphila* MTCC 6724; and
(d) semi conducting particles comprising a precursor metal component, electron facilitator and dye molecule wherein the semi conducting particles are located on cell surface of the electroactive microorganisms.

A further embodiment of the present invention provides a method for bio-assisted conversion of $CO_2$ to fuel precursors employing the semiconducting biogenic hybrid catalyst, said method comprising:
(a) adding the semi-conducting biogenic hybrid catalyst of the invention to culture medium in a transparent reactor;
(b) sparging $CO_2$ through the culture medium and irradiating the transparent reactor with a light source having wavelength >400 nm; and
(c) recovering the fuel precursors from the culture medium.

Yet another embodiment of the present invention provides that the fuel precursors are selected from the group consisting of methanol, ethanol, acetic acid, butanol, isopropanol, butyric acid, and caproic acid.

In another embodiment of the present invention, there is provided a method for bio-assisted conversion of $CO_2$ to fuel precursors employing the semiconducting biogenic hybrid catalyst, said method comprising:
(a) adding the semi-conducting biogenic hybrid catalyst of the invention to culture medium in a transparent reactor;
(b) sparging $CO_2$ through the culture medium and irradiating the transparent reactor with a light source having wavelength >400 nm; and
(c) recovering the fuel precursors from the culture medium;
  wherein the fuel precursors are selected from the group consisting of methanol, ethanol, acetic acid, butanol, isopropanol, butyric acid, and caproic acid.

A further embodiment of the present invention provides a method for bio-assisted conversion of biogas to fuel precursors employing the semiconducting hybrid catalyst said method comprising:
(a) adding the semi-conducting biogenic hybrid catalyst of the invention to culture medium in a glass column;
(b) sparging biogas through the culture medium and irradiating the glass column with a light source having wavelength >400 nm; and
(c) recovering the fuel precursors from the culture medium;
  wherein the fuel precursors comprise a mixture of methanol, ethanol, and acetic acid.

Still another embodiment of the present invention provides a process for synthesizing a semiconductor biogenic-hybrid catalyst, said process comprising:
(a) selectively culturing electroactive microorganisms selected from the group consisting of *Enterobacter aerogenes* MTCC 25016, *Serratia* sp. MTCC 25017, *Shewanella* sp. MTCC 25020, *Alcaligenes* sp. MTCC 25022, *Pseudomonas aeruginosa* MTCC 1036, *Ochrobactrum anthropi* ATCC 49188, *Ochrobactrum anthropi* MTCC 9026, and *Pseudomonas alcaliphila* MTCC 6724;
(b) mixing at least a salt, at least one 2D material, and an electron facilitator, in presence of a surface directing agent to obtain a semiconducting hybrid solution;
(c) adding the semiconducting hybrid solution of step (b) to the electroactive microorganism culture of step (a) to obtain an initiator culture;
(d) providing counter ion precursor to the initiator culture of step (c); and
(e) separating the semiconductor biogenic-hybrid catalyst from the culture;
wherein the salt is selected from the group consisting of $CuCl_2$, $CdCl_2$, $ZnCl_2$, $ZnBr_2$, $GaCl_3$, $InCl_3$, $FeCl_2$, $FeCl_3$, $SnCl_2$, $SnCl_4$, $Cd(NO_3)_2$, $Ga(NO_3)_3$, $Ln(NO_3)_3$, $Zn(NO_3)_2$, $Fe(NO_3)_3$, $CdCO_3$, $CdSO_4$, $FeSO_4$, $ZnSO_4$, $Fe_2O_3$, $CdO$, $Ga_2O_3$, $Ln_2O_3$, $ZnO$, $SnO$, $SnO_2$, $Fe(OH)_3$, $Zn(OH)_2$, $FeOOH$, $FeO(OH)$, $Cd(CH_3COO)_2$, Iron perchlorate, Copper perchlorate, Copper EDTA complex, Nickel alkylamine complex, Iron piperidine complex, Cadmium pyridine complex, Iron bipyridine salt and Iron acac complex;
wherein the 2D material is selected from the group consisting of graphene, porous graphene, $gC_3N_4$, single walled CNT, $MoS_2$, $WS_2$, $SnS_2$, phosphorene, graphene nanoparticles (Gr-Np), TiC, and borophene;
wherein the electron facilitator is selected from the group consisting of neutral red, azo-dyes, Iron porphyrin complex, Schiff base complex, multi walled CNT, Cd (II) or Cu (II) imidazole complex, and Ruthenium complex;
wherein the surface directing agent is selected from the group consisting of Tween, sodium lauryl sulfate, p-172, Lauryl dimethyl amine oxide, Cetyltrimethylammonium bromide, Polyethoxylated alcohol, Polyoxyethylene sorbitan Octoxynol (Triton X100), N, N-dimethyldodecylamine-N-oxide, Hexadecyltrimethylammonium bromide, Polyoxyl 10 lauryl ether, Brij 721, sodium deoxycholate, sodium cholate, Polyoxyl castor oil (Cremophor), Nonylphenol ethoxylate (Tergitol), Cyclodextrins, Lecithin, and Methylbenzethonium chloride (Hyamine); and
wherein the counter ion precursor is a gaseous material or an organosulfur compound.

Another embodiment of the present invention provides that the gaseous material is selected from the group consisting of $H_2S$ containing gas, Industrial flue gas, and bio gas.

A further embodiment of the present invention provides that the organosulfur compound is selected from the group consisting of methanethiol, ethanethiol, propanethiol, butanethiol, thiophenol, ethanedithiol, 1,3ropanedithiol, 1,4 butanedithiol, thiophene, 2-mercaptoethanol, 3-mercaptopropanol, 4mercaptophenol, dithiothreitol, cysteine, homocysteine, methionine, thioserine, thiothreonine, thiotyrosine, glutathione, 2-thiouracil, 6-methyl-2-thiouracil, 4-thiouracil, 2,4dithiouracil, 2-thiocytosine, 5-methyl-2-thiocytosine, 5-fluoro-2-thiocytosine, 2-thiothymine, 4-thiothymine, 2,4- dithiothymine, 6-thioguanine, 8-thioadenine, 2-thioxanthine, 6-thioxanthine, 6-thiohypoxanthine, 6-thiopurine, dimethyl sulfide, diethyl sulfide, diphenyl sulfide, biotin, cystine, lipoic acid, diphenyl disulfide, iron disulfide, 2-hydroxyethyldisulfide, thioacetic acid, trimethylsulfonium, diphenylmethyl sulfonium chloride, dimethylsulfoxide, dimethylsulfone, thioketone, thioamide, thiocyanate, isothiocyanate, thiocarbamate, and dithiocarbamates.

The media composition used for the microbe can be composed of micro nutrients, vitamins such as 0.40 g/L NaCl, 0.40 g/L $NH_4Cl$, 0.33 g/L $MgSO_4 \cdot 7H_2O$, 0.05 g/L $CaCl_2$), 0.25 g/L KCl, 0.64 g/L $K_2HPO_4$, 2.50 g/L $NaHCO_3$, trace mineral (1000.0 mg/L $MnSO_4 \cdot H_2O$, 200.0 mg/L $CoCl_2 \cdot 6H_2O$, 0.2 mg/L $ZnSO_4 \cdot 7H_2O$, 20.0 mg/L $CuCl_2 \cdot 2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L.

The appropriate operational pH of the media has been estimated by varying its pH using phosphate buffer. It has been found that the pH of the system can be varied from 3 to 11. The microbes were found to grow suitably in the pH range without any impact on product formation.

In an embodiment, the temperature of the reaction medium was varied from 25 to 55 and the effect on microbial population and hydrocarbon formation was observed to be essentially unaffected by variation of temperature. In another embodiment, the step of fermentation in the claimed process can be worked even in the dark if a suitable carbon source is provided.

In another embodiment, the present invention can be performed in mixotrophic mode.

In another embodiment, the present invention can be performed in heterotrophic mode.

In another embodiment, different $CO_2$ sources have been used for the bioconversion. The sources of carbon dioxide containing gas may include streams or the atmosphere or water and/or dissolved or solid forms of inorganic carbon, into organic compounds. In these process steps carbon dioxide containing flue gas, or process gas, or air, or inorganic carbon in solution as dissolved carbon dioxide, carbonate ion, or bicarbonate ion including aqueous solutions such as sea water, or inorganic carbon in solid phases such as but not limited to carbonates and bicarbonates, is pumped or otherwise added to a vessel or enclosure containing nutrient media and microorganisms.

Light is an essential substrate for the phototrophic performance of the microbial culture. Both the spectral quality and the intensity of light are important for microbial performance. The light sources can be direct sunlight, LED lights, light sources having wavelength higher than 400 nm. In some embodiments continuous and flashing light was provided to the culture medium. The flashing light was provided in a dark light ratio of 1:5 second. It was found that the overall yield has been significantly enhanced with intermittent light source. So, the continuous light probably saturates the electron confinement in microbes result a decrease in the product formation. On the other hand, the intermittent light is suitable due to fraction of dark-cycle, which is essential for complete use of the electron by the microbe cells.

Semiconductor photo-catalyst is irradiated by solar light and absorbs photon with energy equal to or higher than that of band gap for the semiconductor. Then, photogenerated electron-hole pairs are produced. Photo-generated hole is oxidative while photogenerated electron is reductive. The reductive electron consequently enters into the microbial cell via electron carriers and assists the $CO_2$ reduction process.

In accordance with the present invention, the process of operation of the carbon dioxide reduction process mediated by semiconducting biogenic catalyst can be batch mode or continuous.

In the batch mode, the active culture (5 ml) was centrifuged, washed in phosphate buffer (pH=7.5) and diluted in 1 ml of buffer for semiconducting biogenic catalysts synthesis. The semiconducting biogenic catalysts hybrids were prepared by different routs by varying the metal counter species. 0.2 wt. % metal counter species and 2 mM metal ion (5 ml) were inserted to the serum bottle containing 20 ml of fresh media and 1 ml of microbial culture (phosphate buffer diluted). After an inoculation of 24 h, the culture medium changes color due to formation of semiconducting biogenic catalysts. Similarly, in case of $H_2S$ mediated synthesis, 50 ppm $H_2S$ (balance $N_2$) gas was passed through a filter to 20 ml media containing 2 mM metal ion for 10 second at a rate of 2 ml/min and culture was inoculated for 24 at 30° C.

All photosynthesis measurements were conducted for a conjugative period of 72 h using $CO_2$ as carbon source. In one set of experiment $CO_2$ (99.99%) was purged for 24 h/day in continuous mode in 20 ml/h through filter. Visible light was employed to provide photon flux in continues or intermittent manner. The serum bottle containing the semiconducting biogenic hybrid catalysts was exposed to the light source. 1 ml of the culture from the serum bottle was withdrawn; centrifuged for 5 min at 15,000 rpm and the supernatant was quantified using an Agilent model 6850 gas chromatograph (GC) system equipped with a flame ionization detector (FID), a DB-FFAP capillary column (0.25 mm film thickness), and an automatic injector.

The transfer of electrons to the microbes is the main driving force that can occur either directly from an electrode or indirectly through an electron mediator. When, biogenic hybrid catalyst of the present invention (for instance such as ZnS/g-$C_3N_4$/neutral red *Enterobacter aerogenes* microbe hybrid of Example 1) was synthesized, the total product yield increases significantly due to electron sensing properties of g-$C_3N_4$ and NR. The advantage of the present system is the easiness of the process as the system can work in a standalone manner without any systematic requirement. In case of ZnS/g-$_{C3N4}$/neutral red *Enterobacter aerogenes* microbe hybrid, ZnS acts as a potential electron acceptor and the unique 2D structures and excellent electronic properties of g-C3N4 help in the capability to accept/transport electrons photogenerated from band gap photo excitation of semiconductors upon light irradiation. The neutral red help optimize the photogenerated charge carrier pathway or efficiency across the interface between ZnS and g-C3N4. In other words, under visible light irradiation, the electron hole pairs are generated from semiconductor ZnS due to its band gap photoexcitation. Because of the excellent electron conductivity of the g-C3N4 sheet, the g-C3N4 platform is able to accept and shuttle the photogenerated electrons from ZnS. The presence of NR in the interlayer matrix between ZnS and GR could optimize the photogenerated electron transfer pathway from semiconductor ZnS to the electron conductive g-C3N4, to microbe surface by which the lifetime of charge carriers (electron-hole pairs) is prolonged. This in turn would contribute to the photoactivity improvement of the semiconducting biogenic hybrid catalyst.

Figure 2:
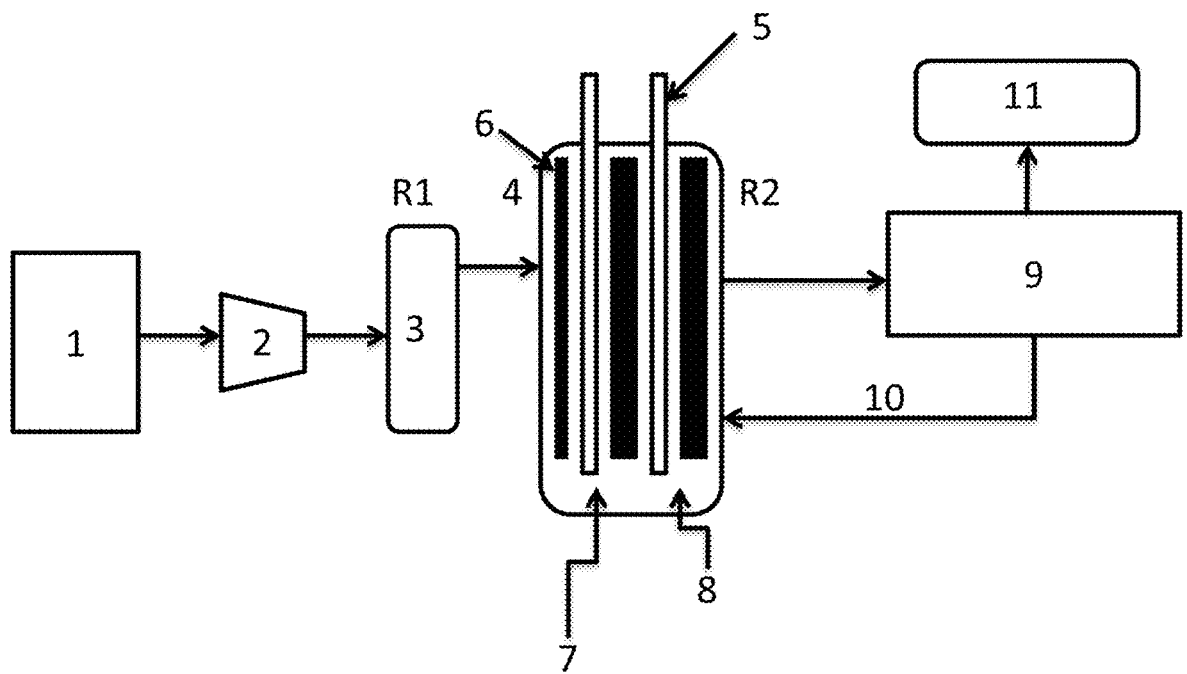
FIG. 2 depicts the schematic representation of continuous system for microbial $CO_2$ reduction in bio-film condition.

For a continuous mode operation, 3 or more different reactors have to operate in parallel as shown in FIG. 2.

a. In rector $R_1$, the microbial culture was prepared in nutrient media. To the media, 0.2 mM salt solution and 0.2 wt % of metal counter species or $H_2S$ gas has been supplied in a continuous process (0.1 ml/min). The formation of semiconducting biogenic hybrid catalysts occurs after 24 h of inoculation at 30° C. The growth of microbial culture of culture has been monitored by OD analysis.

b. In the reactor $R_2$, $CO_2$ hydration occurs by the presence of carbonic anhydrase enzyme immobilized on magnetic foam. The $CO_2$ dissolved solution is continuously supplied to the R2.

c. The cell from the reactor $R_1$ was centrifuged and transferred to the rector $R_3$ till the OD reached to $R_2$. After that the soluble $CO_2$ from reactor R2 was released with a floe rate of 1 ml/Min.

d. To the reactor $R_3$, light source was provided from all sides via continuous or intermittent process. The intermittent light was provided in 1 s:5 s dark and light ratio. The reaction continues for 24 h and the cell was separated from the product by centrifugation and recalculated to reactor R1.

Having described the basic aspects of the present invention, the following non-limiting examples illustrate specific embodiment thereof.

EXAMPLES

Example 1

$CO_2$ Conversion by ZnS/g-$C_3N_4$/Neutral Red *Enterobacter aerogenes* (EA-1) (MTCC 25016)

a. Selection and Culture of Electroactive Microbe

An electro active *Enterobacter aerogenes* (EA-1) (MTCC 25016) microbe was isolated and cultivated in an optimized medium. All glassware and samples were sterilized by autoclaving at 121° C. for 15 min. The media composition was as follows: (0.40 g/L NaCl, 0.40 g/L $NH_4Cl$, 0.33 g/L $MgSO_4 \cdot 7H_2O$, 0.05 g/L $CaCl_2$, 0.25 g/L KCl, 0.64 g/L $K_2HPO_4$, 2.50 g/L $NaHCO_3$, trace mineral (1000.0 mg/L $MnSO_4 \cdot H_2O$, 200.0 mg/L $CoCl_2 \cdot 6H_2O$, 0.2 mg/L $ZnSO_4 \cdot 7H_2O$, 20.0 mg/L $CuCl_2 \cdot 2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L, 0.5% glucose). Cultures were grown at 30° C. Cell growth was monitored by measuring OD at 660 nm with a UV visible spectrophotometer.

b. Preparation of Semi-Conducting Hybrid Solution

ZnS semiconducting particle has been synthesized on the surface of the microbes by passing $H_2S$ in with a flow rate of 10:0.1. Typically, in a 100 ml of deionized water 0.1 mg of g-$C_3N_4$ was dispersed by sonication and 0.2 mM $Zn(NO_3)_2$ was added to it. To the dispersed material 500 μL of Tween 20 was added as a surface directing agent. After 1 h of sonication 0.01 mM Neutral red was added. The material was designated as A. In an autoclaved tube the active microbial culture (5 ml) (CFU=$2.3 \times 10^8$) was centrifuged, washed in phosphate buffer (pH=7.5) and diluted in 1 ml of buffer for microbe-ZnS synthesis. In $H_2S$ mediated biogenic hybrid synthesis, 50 ppm $H_2S$ (balance $N_2$) gas was passed through a filter to 20 ml media containing 4 ml of A for 30 second at a rate of 0.1 ml/min and the light whitish solution obtained was inoculated for 24 at 30° C.

c. Analysis of Biogenic Hybrid Catalyst

All photosynthesis measurements were conducted for a conjugative period of 5 days using $CO_2$ as carbon source. In one set of experiment, $CO_2$ (99.99%) was purged for 5 h/day in continuous mode in 20 ml/h through filter. Visible light of wavelength t ($\lambda$>400 nm) was employed to provide photon flux. Provision has been made to provide light at different conditions to the biogenic hybrid catalyst to utilize $CO_2$ in their metabolic activity. In one set of experiments, constant solar light was given for 24 h and in another set, intermittent light source was given with light:dark ratio of 1:3 s. 1 ml of the culture form the serum bottle were withdrawn from time to time; centrifuged for 5 min at 15,000 rpm and the supernatant were quantified using an Agilent model 6850 gas chromatograph (GC) system equipped with a flame ionization detector (FID), a DB-FFAP capillary column (0.25 mm film thickness), and an automatic injector.

First of all, the viability determined by colony-forming units (CFU) assays for 5 days (from the initial $5.9 \pm 0.4 \times 10^9$ CFU $ml^{-1}$ to $1.7 \pm 0.4 \times 10^9$ cells $ml^{-1}$), indicating that the ZnS/g-$C_3N_4$/neutral red *Enterobacter aerogenes* microbe hybrid system has potential ability for sustainable growth with the experimental condition.

d. Analysis of Hydrocarbon Conversion by the Biogenic Hybrid Catalyst

Figure 3:
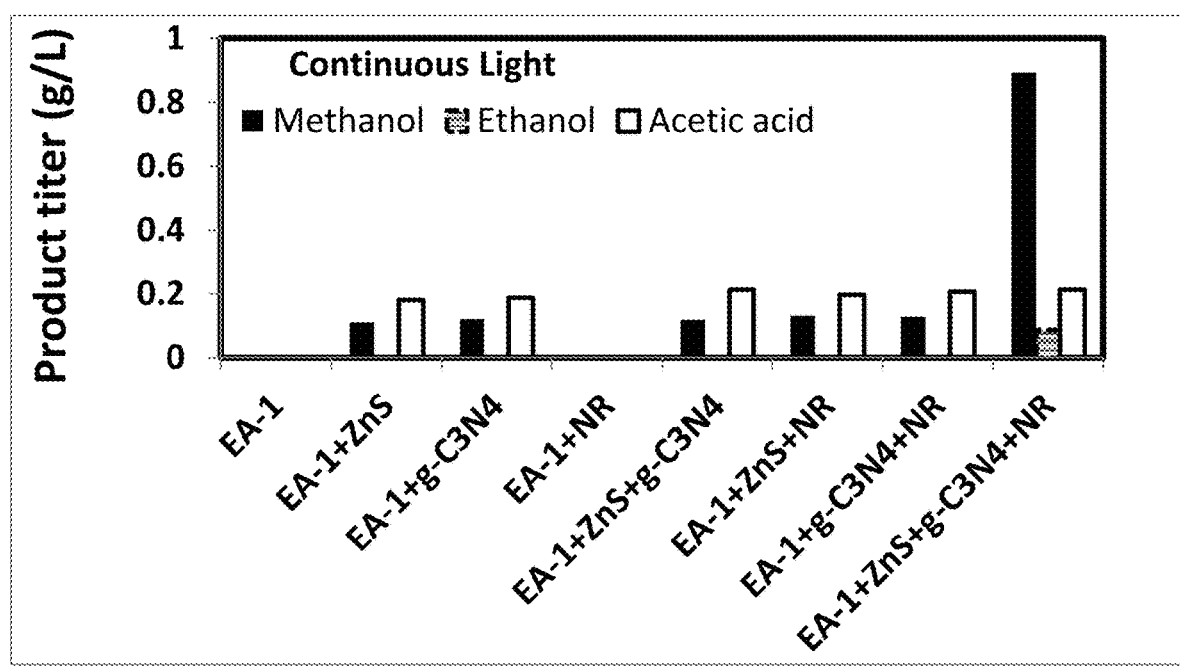
FIG. 3 depicts the graphical representation of $CO_2$ conversion to fuels and chemicals by ZnS/g-C3N4/neutral red *Enterobacter aerogenes* under continuous light irradiation. Here, EA-1 is designated for *Enterobacter aerogenes*.
Figure 4:
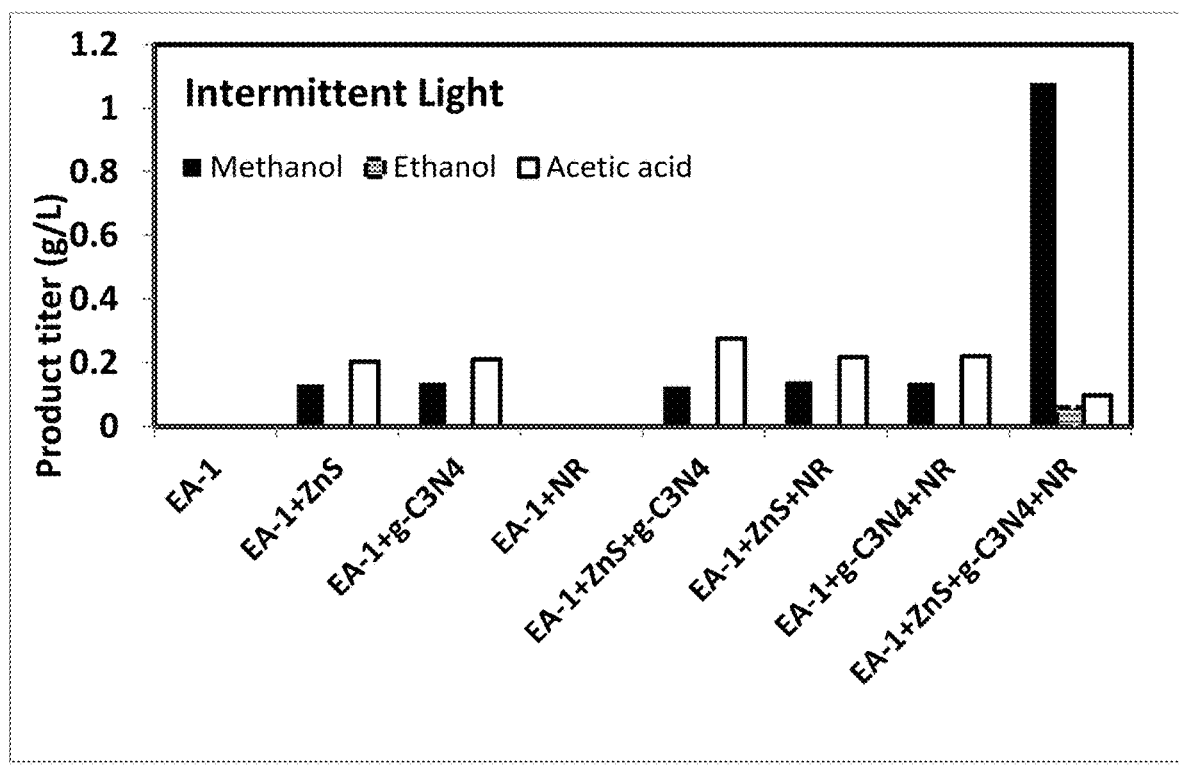
FIG. 4 depicts the graphical representation of $CO_2$ conversion to fuels and chemicals by ZnS/g-$C_3N_4$/neutral red *Enterobacter aerogenes* under intermittent light irradiation. Here, EA-1 is designated for *Enterobacter aerogenes*.
Figure 5:
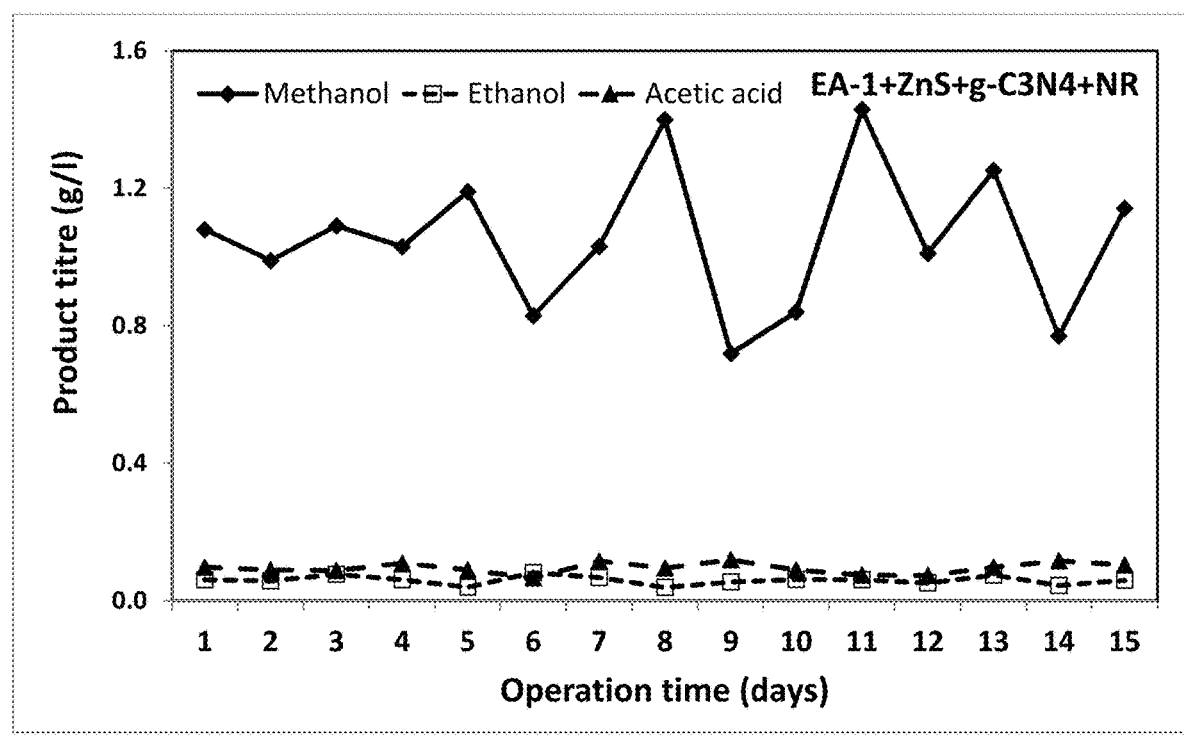
FIG. 5 depicts the line graph of product profile for continuous $CO_2$ reduction system in intermittent light radiation condition.

To confirm solar to fuel and hydrocarbon conversion by ZnS/g-$C_3N_4$/neutral red *Enterobacter aerogenes* microbe hybrid, a series of control experiments was carried out in which microbe ZnS, and light were systematically removed. In the absence of light no product formation happens. However, when light was given (both constant and intermittent) a series of single and multiple carbon products are obtained: methanol, ethanol, acetic acid. When controlled experiments were carried out using only *Enterobacter aerogenes* no product formation was observed in both continuous and intermittent light indicating that the microbes are non-photosynthetic. Several stringent controls with different combinations have been tried as shown in the FIG. 5. It has been found that a very low concentration of methanol, acetic acid have been obtained in the controlled condition for both constant and intermittent light condition. However, product formation surprising enhanced when the semiconducting biogenic hybrid catalyst composed of *Enterobacter aerogenes*+ZnS+g-$C_3N_4$+NR has been used. 0.89 g/L of methanol, 0.087 g/L ethanol and 0.213 g/L acetic acid were obtained under constant light source (FIG. 3). There is a significantly product enhancement: 1.080 g/L of methanol, 0.061 g/L ethanol and 0.098 g/L acetic acid in intermittent light source (FIG. 5). The detailed experimental conditions are presented in Table 1.

TABLE 1

| Experimental conditions | |
|---|---|
| Bio-hybrid | ZnS/g-$C_3N_4$/neutral red *Enterobacter aerogenes* microbe hybrid |
| Temperature | 30° C. |
| $CO_2$ flow rate | 1 ml/min |
| Final Product | 0.89 g/L of methanol, 0.087 g/L ethanol |

TABLE 1-continued

| Experimental conditions | |
|---|---|
| (Constant light source) | and 0.213 g/L acetic acid |
| Final Product (Intermittent light source) | 1.080 g/L of methanol, 0.061 g/L ethanol and 0.098 g/L acetic acid |

Example 2

$CO_2$ Conversion by $SnS/MoS_2/CNT$ Shewanella sp. (EA-2) (MTCC 25020)

For continuous mode of operation, three reactor systems have been used as shown in FIGS. 2 and 3.

a. Selection and Culture of Electroactive Microbe

As directed in the example-1, the Shewanella sp. (EA-2) (MTCC 25020) Microbes were grown in the reactor $R_1$ composed of media 0.40 g/L NaCl, 0.40 g/L $NH_4Cl$, 0.33 g/L $MgSO_4 \cdot 7H_2O$, 0.05 g/L $CaCl_2$, 0.25 g/L KCl, 0.64 g/L $K_2HPO_4$, 2.50 g/L $NaHCO_3$, trace mineral (1000.0 mg/L $MnSO_4 \cdot H_2O$, 200.0 mg/L $CoCl_2 \cdot 6H_2O$, 0.2 mg/L $ZnSO_4$ $7H_2O$, 20.0 mg/L $CuCl_2 \cdot 2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L.

b. Preparation of the Semiconducting Hybrid Solution

In another vessel, the semiconducting hybrid was prepared by adding 0.2 mM $SnCl_2$, 0.1 g $MoS_2$ and 500 µL single walled CNT solutions (2 mg/ml) in 100 ml of deionised water. To the solution 0.1 ml of Tween 20 was added as surface directing agent. The whole solution was sonicated for 1 h to obtain a homogeneously dispersed solution. The solution was autoclaved at 100° C. for 15 min and designated as A.

To the react $R_1$ containing microbial culture, solution A was supplied at a flow rate of 0.1 ml/min. At the same time, $H_2S$ gas has been supplied in a continuous process (0.1 ml/min). The formation of semiconducting biogenic hybrid catalysts occurs after 24 h of inoculation at 30° C. The growth of $SnS/MoS_2/CNT$ Shewanella sp. microbe hybrid microbial culture of has been monitored by OD analysis.

c. Analysis of Biogenic Hybrid Catalyst $SnS/MoS_2/CNT$ Shewanella sp. microbes hybrid has been characterized using electron microscopic studies. The SnS act as a biocompatible semiconductor to harvest sunlight. The $MoS_2$ as an efficient 2D material helps in electron transfer and hence reduces the electron-hole recombination. The CNT (multi walled) here act as a facilitator to transfer electron form the semiconductor hybrid to cell of the microbes.

In the reactor $R_2$, $CO_2$ hydration occurs by the presence of carbonic anhydrase enzyme immobilized on magnetic foam. The $CO_2$ (99.999%) was supplied to the reactor from below at a flow rate of 1 ml/min and the reactor contain immobilized CA. The $CO_2$ dissolved solution is continuously supplied to the $R_2$ with a flow rate of 0.5 ml/min.

The cell from the reactor $R_1$ was centrifuged and transferred to the rector $R_3$ till the OD reached a value of 2 in $R_2$. The reactor has been stirred continuously at 300 rpm. After that the soluble $CO_2$ from reactor $R_2$ was released to reactor $R_3$ with a flow rate of 1 ml/Min.

To the reactor $R_3$, light source was provided from all sides via continuous or intermittent process. The intermittent light was provided in 1 s:5 s dark and light ratios. The reaction continues for 15 consecutive days and in each 24 h the cells were separated from the product by centrifugation and recalculated to reactor $R_1$.

d. Analysis of Hydrocarbon Conversion by the Biogenic Hybrid Catalyst

Figure 6:
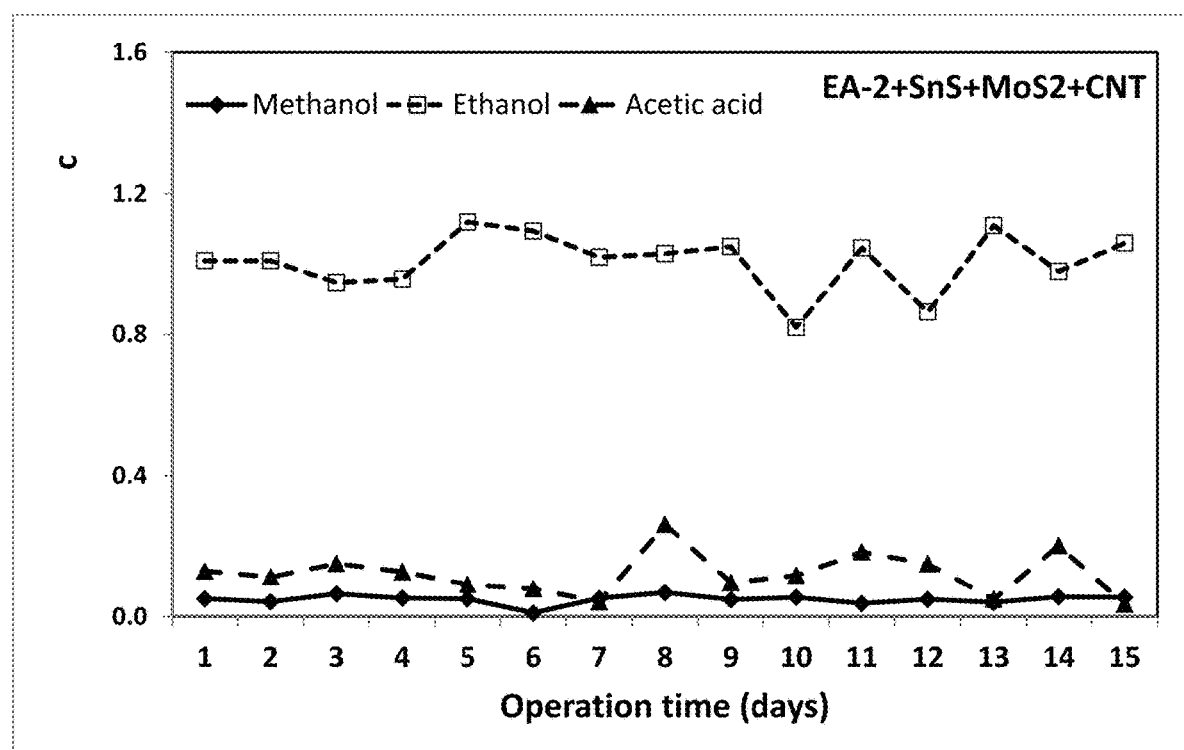
FIG. 6 depicts the line graph of product profile for continuous $CO_2$ reduction system in intermittent light radiation condition. Here, EA-2 is designated for *Shewanella* sp.
Figure 7:
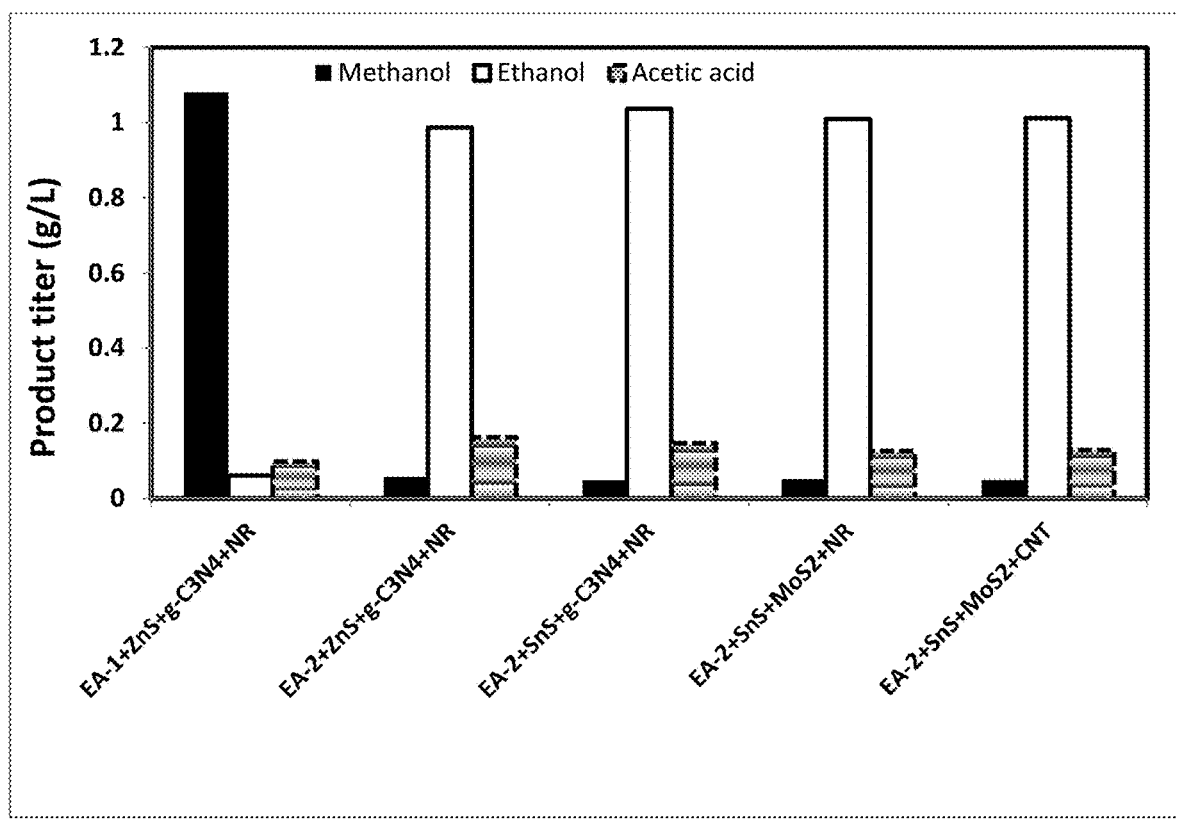
FIG. 7 depicts the graphical representation of product profile obtained at different microbe, semiconducting, 2D material and electron facilitator condition. Here, EA-1 and EA-2 are designated for *Enterobacter aerogenes* and *Shewanella* sp., respectively.

From the product profile (FIGS. 5 &6), it was found that the formation of the product varies according to the microbe used. In case of semiconducting biogenic hybrid catalyst containing $ZnS/g-C_3N_4$/neutral red Enterobacter aerogenes (EA-1), methanol has been obtained as the prominent product (~1.05 g/L/day) in intermittent light condition. At the same time, formation of lower condition of acetic acid (~0.095 g/L/day) and ethanol (~0.06 g/L/day) were also observed. However, using a different semiconducting biogenic hybrid catalyst $SnS/MoS_2/CNT$ Shewanella sp. (EA-2) (at same condition), ethanol has been the prominent product (~1.00 g/L/day) along with low concentration of methanol (0.048 g/L/day and acetic acid (0.12 g/L/day). Furthermore, it has been observed that the concentration of product varies depending on the electro active microbe, semiconducting material, 2D material, electron facilitator used. A comparative table of product formation is included in the FIG. 7.

TABLE 2

| Experimental conditions | | |
|---|---|---|
| Bio-hybrid | $ZnS/g-C_3N_4$/neutral red Enterobacter aerogenes microbe hybrid (EA-1) | $SnS/MoS_2/CNT$ Shewanella sp. (EA-2) |
| Temperature | 30° C. | 30° C. |
| $CO_2$ flow rate | 1 ml/min | 1 ml/min |
| Final Product (Intermittent light source) | 1.080 g/L of Methanol, 0.061 g/L Ethanol, and 0.098 g/L Acetic Acid | Ethanol (~1.00 g/L/day), Methanol (0.048 g/L/day), and Acetic Acid (0.12 g/L/day). |

Example 3

$CO_2$ Conversion by $ZnS/MoS_2/CNT$ Serratia sp (EA-2) (MTCC 25017)

a. Selection and Culture of Electroactive Microbe

An electro active Serratia sp. (EA-2) (MTCC 25017) microbe was isolated and cultivated in an optimized medium. All glassware and samples were sterilized by autoclaving at 121° C. for 15 min. The media composition was as follows: (0.40 g/L NaCl, 0.40 g/L $NH_4Cl$, 0.33 g/L $MgSO_4 \cdot 7H_2O$, 0.05 g/L $CaCl_2$, 0.25 g/L KCl, 0.64 g/L $K_2HPO_4$, 2.50 g/L $NaHCO_3$, trace mineral (1000.0 mg/L $MnSO_4 \cdot H_2O$, 200.0 mg/L $CoCl_2 \cdot 6H_2O$, 0.2 mg/L $ZnSO_4 \cdot 7H_2O$, 20.0 mg/L $CuCl_2 \cdot 2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L, 0.5% glucose). Cultures were grown at 30° C. Cell growth was monitored by measuring OD at 660 nm with a UV visible spectrophotometer.

b. Preparation of the Semiconducting Hybrid Solution

In another vessel, the semiconducting hybrid solution was prepared by adding 0.2 mM $ZnCl_2$, 0.1 g $MoS_2$ and 0.1 mg multi walled CNT in 100 ml of deionised water. To the solution 0.2 mg p-172 surfactant was added. The whole solution was sonicated for 30 min to obtain a homogeneously dispersed solution. The solution was autoclaved at 121° C. for 15 min.

To 1 ml of the fully grown (CFU=2.3*10$^8$) *Serratia* sp culture, 4 ml of autoclaved semiconducting hybrid solution was added and incubated at 35° C. for 24 h. At the same time, $CO_2$ and $H_2S$ were purged to the media with a flow rate of 10:0.1 as per the procedure provided in example 1. Slowly the color of the medium (after 48 h) was changed to pale white indicating the formation of $ZnS/MoS_2$/CNT *Serratia* sp. hybrid. The growth of the microbe hybrid was also monitored by OD analysis.

c. Analysis of Biogenic Hybrid Catalyst

The $ZnS/MoS_2$/CNT *Serratia* sp. hybrid was then exposed to both constant and intermittent light source ($\lambda$>420 nm) (5 s light and 2 second dark). The product was analyzed after each 3 hour by GC. The product profile is provided in Table 3.

Example 4

$CO_2$ Conversion by $CdS/ZnS/g-C_3N_4$ *Alcaligenes* sp. (MTCC 25022)

a. Selection and Culture of Electroactive Microbe

An electro active *Alcaligenes* sp. (MTCC 25022) microbe was isolated and cultivated in an optimized medium. All glassware and samples were sterilized by autoclaving at 121° C. for 15 min. The media composition was as follows: (0.40 g/L NaCl, 0.40 g/L $NH_4Cl$, 0.33 g/L $MgSO_4 \cdot 7H_2O$, 0.05 g/L $CaCl_2$, 0.25 g/L KCl, 0.64 g/L $K_2HPO_4$, 2.50 g/L $NaHCO_3$, trace mineral (1000.0 mg/L $MnSO_4 \cdot H_2O$, 200.0 mg/L $CoCl_2 \cdot 6H_2O$, 0.2 mg/L $ZnSO_4 \cdot 7H_2O$, 20.0 mg/L $CuCl_2 \cdot 2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L, 0.5% glucose). Cultures were grown at 30° C. Cell growth was monitored by measuring OD at 660 nm with a UV visible spectrophotometer.

b. Preparation of the Semiconducting Hybrid Solution

In another vessel, the semiconducting hybrid was prepared by adding 0.2 mM $CdCl_2$, 0.2 mM $ZnCl_2$, 0.1 g $g-C_3N_4$ and 0.1 g Neutral red in 100 ml of deionised water. To the solution Lauryl dimethyl amine oxide (0.2 mg) was added to act as the surface directing agent. The whole solution was sonicated for 30 min to obtain a homogeneously dispersed solution. The solution was autoclaved at 121° C. for 15 min.

To 1 ml of the (CFU=2.3*10$^8$) *Alcaligenes* sp. culture, 100 ml of autoclaved $g-C_3N_4/Zn^+/Cd^{2+}$ was added and incubated at 35° C. for 24 h. At the same time, $CO_2$ and $H_2S$ were purged to the media with a flow rate of 10:0.1 as per the procedure provided in example 1. Slowly the color of the medium (after 48 h) was changed to pale white indicating the formation of $gC_3N_4/CdS/ZnS$ *Alcaligenes* sp. hybrid. The growth of the microbe hybrid was also monitored by OD analysis.

c. Analysis of Biogenic Hybrid Catalyst

The $gC_3N_4/CdS/ZnS$ *Alcaligenes* sp. hybrid was then exposed to intermittent light source (5 s light and 2 second dark). The product was analyzed after each 3 hour by GC. The product profile is provided in Table 3.

Example 5

$CO_2$ Conversion by $CdS/TiC/g-C_3N_4$ *Pseudomonas aeruginosa* (MTCC-1036)

a. Selection and Culture of Electroactive Microbe

An electro active *Pseudomonas aeruginosa* (MTCC-1036) microbe was isolated and cultivated in an optimized medium. All glassware and samples were sterilized by autoclaving at 121° C. for 15 min. The media composition was as follows: (0.40 g/L NaCl, 0.40 g/L $NH_4Cl$, 0.33 g/L $MgSO_4 \cdot 7H_2O$, 0.05 g/L $CaCl_2$, 0.25 g/L KCl, 0.64 g/L $K_2HPO_4$, 2.50 g/L $NaHCO_3$, trace mineral (1000.0 mg/L $MnSO_4 \cdot H_2O$, 200.0 mg/L $CoCl_2 \cdot 6H_2O$, 0.2 mg/L $ZnSO_4 \cdot 7H_2O$, 20.0 mg/L $CuCl_2 \cdot 2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L, 0.5% glucose). Cultures were grown at 30° C. Cell growth was monitored by measuring OD at 660 nm with a UV visible spectrophotometer.

b. Preparation of the Semiconducting Hybrid Solution

In another vessel, the semiconducting hybrid was prepared by adding 0.1 mg of $g-C_3N_4$ and 0.1 mg of nano TiC in a 100 ml of deionized water followed by dispersing by sonication for 1 h. Subsequently, 0.2 mM $CdCl_2$ was also added to the solution and subjected to further dispersion for 30 minutes. To the solution 0.2 mg Polyethoxylated alcohol was added to act as the surface directing agent. The whole solution was sonicated for 30 min to obtain a homogeneously dispersed solution. The solution was autoclaved at 121° C. for 15 min.

To 1 ml of the (CFU=2.3*10$^8$) *Pseudomonas aeruginosa* culture, 100 ml of autoclaved $g-C_3N_4/TiC/Cd^{2+}$ was added and incubated at 35° C. for 24 h. At the same time, $CO_2$ and $H_2S$ were purged to the media with a flow rate of 10:0.1 as per the procedure provided in example 1. Slowly the color of the medium (after 48 h) was changed to pale white indicating the formation of $gC_3N_4/CdS/TiC$ *Pseudomonas aeruginosa* hybrid. The growth of the microbe hybrid was also monitored by OD analysis.

c. Analysis of Biogenic Hybrid Catalyst

The gC$_3$N$_4$/CdS/TiC *Pseudomonas aeruginosa* hybrid was then exposed to intermittent light source (5 s light and 2 second dark). The pH of the medium was maintained at 7.0 using phosphate buffer. The product was analyzed after each 3 hour by GC. The product profile is provided in Table 3.

Example 6

CO$_2$ Conversion by CdS/TiC/Gr-Np *Ochrobactrum anthropi* Microbes (MTCC-9026)

a. Selection and Culture of Electroactive Microbe

An electro active *Ochrobactrum anthropi* microbe (MTCC 9026) was isolated and cultivated in an optimized medium. All glassware and samples were sterilized by autoclaving at 121° C. for 15 min. The media composition was as follows: (0.40 g/L NaCl, 0.40 g/L NH$_4$Cl, 0.33 g/L MgSO$_4$·7H$_2$O, 0.05 g/L CaCl$_2$), 0.25 g/L KCl, 0.64 g/L K$_2$HPO$_4$, 2.50 g/L NaHCO$_3$, trace mineral (1000.0 mg/L MnSO$_4$·H$_2$O, 200.0 mg/L CoCl$_2$·6H$_2$O, 0.2 mg/L ZnSO$_4$·7H$_2$O, 20.0 mg/L CuCl$_2$·2H$_2$O, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L, 0.5% glucose). Cultures were grown at 30° C. Cell growth was monitored by measuring OD at 660 nm with a UV visible spectrophotometer.

b. Preparation of the Semiconducting Hybrid Solution

In another vessel, the semiconducting hybrid was prepared by adding 0.1 mg of Graphene Nanoparticles (Gr-Np) and 0.1 mg of nano TiC in a 100 ml of deionized water followed by dispersing by sonication for 1 h. Subsequently, 0.2 mM CdCl$_2$ was also added to the solution and subjected to further dispersion for 30 minutes. To the solution 0.1 mg Ruthenium complex as electron facilitator and 0.2 mg sodium lauryl sulfate was added to act as the surface directing agent. The whole solution was sonicated for 30 min to obtain a homogeneously dispersed solution. The solution was autoclaved at 121° C. for 15 min.

To 1 ml of the (CFU=2.3*10$^8$) *Ochrobactrum anthropi* culture, 100 ml of autoclaved Gr-Np/TiC/Cd$^{2+}$ was added and incubated at 35° C. for 24 h. At the same time, CO$_2$ and H$_2$S were purged to the media with a flow rate of 10:0.1 as per the procedure provided in example 1. Slowly the color of the medium (after 48 h) was changed to pale white indicating the formation of Gr-Np/CdS/TiC *Ochrobactrum anthropi* hybrid. The growth of the microbe hybrid was also monitored by OD analysis.

c. Analysis of Biogenic Hybrid Catalyst

The Gr-Np/CdS/TiC *Ochrobactrum anthropi* hybrid was then exposed to intermittent light source (5 s light and 2 second dark). The pH of the medium was maintained at 7.0 using phosphate buffer. The product was analyzed after each 3 hour by GC. The product profile is provided in Table 3.

TABLE 3

| Experimental Condition | End Products | | | | | | |
|---|---|---|---|---|---|---|---|
| | Methanol | Ethanol | Acetic acid | Butanol | Isopropanol | Butyric acid | Caproic acid |
| ZnS/MoS$_2$/CNT *Serratia* sp (EA-2) (MTCC 25017) | 0.64 | 0.54 | 0.36 | ND | ND | 0.14 | ND |
| CdS/ZnS/g-C3N4 *Alcaligenes* sp. (MTCC 25022) | ND | 1.28 | 0.96 | 1.14 | ND | 0.81 | 0.16 |
| CdS/TiC/g-C$_3$N$_4$ *Pseudomonas aeruginosa* (MTCC-1036) | 1.78 | ND | 1.13 | ND | 0.66 | 1.41 | 0.12 |
| CdS/TiC/Gr-Np *Ochrobactrum anthropi* microbes (MTCC-9026) | ND | ND | 0.98 | 0.41 | 0.97 | 0.89 | 0.33 |

Example 7

CO$_2$ Conversion Using Combination of Microbe and Salt and One 2D Material a. Different combinations of semi-conducting biogenic hybrid catalysts were synthesized and final products were analyzed by using a similar method as described in example-1.
b. During the synthesis of semi-conducting biogenic hybrid catalysts, two or more salts, 2D materials and electron facilitators were added, whenever required, in equimolar quantities so that the final concentration were same as described in example-1.
c. The temperature for all the experiments were fixed at 30° C. and CO$_2$ flow rate at 1 ml/min
d. Intermittent light source (wavelength >400 nm) was used to carry out all the experiments.
e. The product concentration were given in the Table 4

TABLE 4

| Microbe | Salt | 2D material | Electron facilitator | Yield of the product (g/L/Day) | | | | | | |
|---|---|---|---|---|---|---|---|---|---|---|
| | | | | Methanol | Ethanol | Acetic acid | Butanol | Isopropanol | Butyric acid | Caproic acid |
| *Pseudomonas alcaliphila* MTCC-6724 | — | — | — | ND | ND | ND | ND | ND | ND | ND |
| *Pseudomonas alcaliphila* MTCC-6724 | GaCl$_3$ | WS2 | Ruthenium complex | 0.016 | 1.06 | 0.21 | 0.44 | ND | ND | ND |
| *Pseudomonas alcaliphila* MTCC-6724 | GaCl3 | — | Ruthenium complex | ND | ND | ND | ND | ND | ND | ND |
| *Pseudomonas alcaliphila* MTCC-6724 | GaCl3 | WS2 | — | ND | ND | ND | ND | ND | ND | ND |
| *Pseudomonas alcaliphila* MTCC-6724 | — | WS2 | Ruthenium complex | ND | ND | ND | ND | ND | ND | ND |
| *Ochrobactrum anthropi* ATCC 49188 | InCl3 + ZnCl2 | SnS2 | Cu(II) Imidazole complex | ND | 0.68 | 0.96 | 1.12 | ND | 0.24 | ND |
| *Ochrobactrum anthropi* ATCC 49188 | SnCl4 + FeCl3 | borophene | Iron Prophyrin complex | ND | ND | 1.16 | 0.32 | 0.98 | 1.21 | 0.24 |
| *Enterobacter aerogenes* (EA-1) MTCC 25016 | Fe2O3 + ZnO + CdO | borophene | Multiwalled CNT | ND | 1.41 | 1.16 | 1.08 | ND | 0.74 | 0.22 |
| *Enterobacter aerogenes* (EA-1) MTCC 25016 | In2O3 | MoS$_2$ + WS2 | Iron Shiffbase complex | ND | 1.56 | 1.02 | 1.34 | ND | 0.98 | 0.26 |
| *Pseudomonas aeruginosa* MTCC-1036 | ZnO | Phosphorene + SnS$_2$ | Iron Shiffbase complex | 1.81 | ND | 1.44 | ND | 0.62 | 1.63 | 0.11 |
| *Alcaligenes sp.* MTCC 25022 | ZnBr$_2$ | MoS$_2$ | Iron Shiffbase complex + Ruthenium complex | ND | 1.32 | 0.92 | 1.16 | ND | 0.76 | 0.14 |
| *Alcaligenes sp.* MTCC 25022 | SnO | Porous graphene | Cd (II)-Imidazole complex + Iron Prophyrin complex | ND | 1.26 | 1.14 | 1.18 | ND | 0.94 | 0.21 |

Example 8

Use of Raw Biogas as Feedstock

The following example describes the use of biogas as feedstock which may be used as a process for up gradation of biogas along with $CO_2$ conversion to valuable products using present invention.

a. Selection and Culture of Electroactive Microbe

An electro active *Serratia* sp (EA-2) (MTCC 25017) was cultivated in an optimized medium. All glassware and samples were sterilized by autoclaving at 121° C. for 15 min. The media composition was as follows: (0.60 g/L NaCl, 0.20 g/L $NH_4Cl$, 0.35 g/L $MgSO_4·7H_2O$, 0.09 g/L $CaCl_2$), trace mineral (1000.0 mg/L $MnSO_4·H_2O$, 200.0 mg/L $CoCl_2·6H_2O$, 0.2 mg/L $ZnSO_4·7H_2O$, 20.0 mg/L $CuCl_2·2H_2O$, 2000.0 mg/L Nitriloacetic acid), and vitamin (Pyridoxine·HCl 10.0 mg/L, Thiamine·HCl 5.0 mg/L, Riboflavin 5.0 mg/L, Nicotinic acid 5.0 mg/L, Biotin 2.0 mg/L, Folic acid 2.0 mg/L, Vitamin B12 0.1 mg/L, 0.5% glucose). Cultures were grown at 30° C. Cell growth was monitored by measuring OD at 660 nm with a UV visible spectrophotometer.

b. Preparation of the Semiconducting Hybrid Solution

In another vessel, the semiconducting hybrid was prepared by adding 0.1 mg of graphene nanoparticles (Gr-Np) and 0.1 mg of nano TiC in a 100 ml of deionized water followed by dispersing by sonication for 1 h. Subsequently, 0.2 mM $CdCl_2$ was also added to the solution and subjected to further dispersion for 30 minutes. To the solution 0.1 mg Ruthenium complex as electron facilitator and 0.2 mg sodium lauryl sulfate was added to act as the surface directing agent. The whole solution was sonicated for 30 min to obtain a homogeneously dispersed solution. The solution was autoclaved at 121° C. for 15 min. To 1 ml of the (CFU=$2.2\times10^8$) *Serratia* sp (EA-2) (MTCC 25017), 250 ml of autoclaved Gr-Np/TiC/$Cd^{2+}$ was added and incubated at 35° C. for 24 h.

c. Use of Raw Biogas as $CO_2$ and $H_2S$ Source 250 ml of Gr-Np/CdS/TiC *Serratia* sp (EA-2) was placed in a glass column (0.5 meter). Raw biogas having composition 60% $CH_3$, 40% $CO_2$ and 300 ppm $H_2S$ were purged to the media with a flow rate of 1 ml/min with an retention time of 650 second. The column was exposed to intermittent light source (5 s light and 2 second dark). The pH of the medium was maintained at 7.0 using phosphate buffer.

d. Analysis of Product

The gas outlet was collected in a tedlar bag and analyzed by GC. The result shows an outlet gas concentration with 98% $CH_3$ and 2% $CO_2$.

5 ml of product from column reactor was collected after 24 h, centrifuged and was analyzed by GC. It was found that with intermittent light 1.87 g/L of methanol, 0.61 g/L ethanol and 0.95 g/L acetic acid were obtained.

The electroactive microorganisms, *Serratia* sp. MTCC 25017 and *Shewanella* sp. MTCC 25020, were deposited on Apr. 9, 2015 at MTCC (Microbial Type Culture Collection) of the Institute of Microbial Technology, Chandigal-160 036, Sector 39-A, Republic of India.

The invention claimed is:

1. A method for bio-assisted conversion of $CO_2$ to fuel precursors employing a semiconducting biogenic hybrid catalyst, the method comprising:

selectively culturing of an electroactive microorganism, wherein the electroactive microorganism is *Shewanella* sp. MTCC 25020;

mixing at least one salt containing a metal ion, at least one 2D material, and an electron facilitator in presence of a surfactant to obtain a semiconducting hybrid solution, wherein the at least one salt containing the metal ion is selected from the group consisting of $CuCl_2$, $CdCl_2$, $ZnCl_2$, $ZnBr_2$, $GaCl_3$, $InCl_3$, $FeCl_2$, $FeCl_3$, $SnCl_2$, $SnCl_4$, $Cd(NO_3)_2$, $Ga(NO_3)_3$, $Ln(NO_3)_3$, $Zn(NO_3)_2$, $Fe(NO_3)_3$, $CdCO_3$, $CdSO_4$, $FeSO_4$, $ZnSO_4$, $Fe_2O_3$, $CdO$, $Ga_2O_3$, $Ln_2O_3$, $ZnO$, $SnO$, $SnO_2$, $Fe(OH)_3$, $Zn(OH)_2$, $FeOOH$, $FeO(OH)$, $Cd(CH_3COO)_2$, Iron perchlorate, Copper perchlorate, Copper EDTA complex, Nickel alkylamine complex, Iron piperidine complex, Cadmium pyridine complex, Iron bipyridine salt and Iron acac complex, wherein the 2D material is selected from the group consisting of graphene, porous graphene, graphene nanoparticles, single walled CNT, and TiC, wherein the electron facilitator is selected from the group consisting of neutral red, azo-dyes, iron porphyrin complex, Schiff base complex, multi walled CNT, Cd (II) or Cu (II) imidazole complex, and Ruthenium complex, and wherein the surfactant is selected from the group consisting of sodium lauryl sulfate, Lauryl dimethyl amine oxide, Cetyltrimethylammonium bromide, Polyethoxylated alcohol, Polyoxyethylene sorbitan Octoxynol, N, N-dimethyldodecylamine-N-oxide, Hexadecyltrimethylammonium bromide, Polyoxyl 10 lauryl ether, sodium deoxycholate, sodium cholate, Polyoxyl castor oil, Nonylphenol ethoxylate, Cyclodextrins, Lecithin, and Methylbenzethonium chloride;

adding the semiconducting hybrid solution to the electroactive microorganism culture to obtain an initiator culture;

providing a counter ion precursor to the initiator culture to form a semi-conducting biogenic hybrid catalyst to obtain a mixed culture, wherein the counter ion precursors are organosulfur compounds, wherein the organosulfur compounds are selected from the group consisting of hydrocarbon mercaptans, alcohol containing mercaptans, mercapto amino acids, mercapto peptides, mercaptopyrimidines, mercapto purines, thioethers, disulfides, thiocarboxylic acids, thioesters, sulfonium salts, sulfoxides, sulfones, thioketones, thioamides, thiocyanates, isothiocyanates, thiocarbamates, and dithiocarbamates;

separating the semi-conducting biogenic-hybrid catalyst from the mixed culture;

adding the semi-conducting biogenic hybrid catalyst to a culture medium in a transparent reactor, wherein the semi-conducting biogenic hybrid catalyst consists of the electroactive microorganism, and semi conducting particles, wherein the semi conducting particles consist of a precursor metal component, the electron facilitator, the at least one 2D material, the surfactant, and the counter ion precursor, wherein the semi conducting particles are located on a cell surface of the electroactive microorganism, wherein the precursor metal component is selected from the group consisting of a metal halide, a metal nitrate, a metal perchlorate, a metal carbonate, a metal sulfate, a metal oxide, a metal hydroxide, a metal oxyhydroxide, an iron and copper EDTA complex, metal amines or bipyridine salt complex of iron, zinc and nickel, a metal carboxylate, and a metal acetylacetonate complex of iron, copper, cadmium, and nickel;

sparging the CO₂ through the culture medium and irradiating the transparent reactor with a light source; and recovering the fuel precursors from the culture medium;

wherein the fuel precursors are selected from the group consisting of methanol, ethanol, acetic acid, butanol, isopropanol, butyric acid, and caproic acid.

2. The method of claim 1, wherein the $CO_2$ is sourced from a carbon dioxide containing flue gas, a process gas, or air; an inorganic carbon as dissolved carbon dioxide, a carbonate ion, or a bicarbonate ion in aqueous solutions; or an inorganic carbon in solid phases as carbonates and bicarbonates.

3. The method of claim 1, wherein the method is performed in a batch mode or in a continuous mode.

4. The method of claim 3, wherein for the continuous mode is carried out in a plurality of reactors, wherein the plurality of reactors is placed parallel to each other.

5. The method of claim 1, wherein the light source is an intermittent light source.

6. A method for bio-assisted conversion of a biogas to fuel precursors employing a semiconducting hybrid catalyst, the method comprising:

selectively culturing of an electroactive microorganism, wherein the electroactive microorganism is *Shewanella* sp. MTCC 25020 or *Serratia* sp. MTCC 25017;

mixing at least one salt containing a metal ion, at least one 2D material, and an electron facilitator in presence of a surfactant to obtain a semiconducting hybrid solution, wherein the at least one salt containing the metal ion is selected from the group consisting of $CuCl_2$, $CdCl_2$, $ZnCl_2$, $ZnBr_2$, $GaCl_3$, $InCl_3$, $FeCl_2$, $FeCl_3$, $SnCl_2$, $SnCl_4$, $Cd(NO_3)_2$, $Ga(NO_3)_3$, $Ln(NO_3)_3$, $Zn(NO_3)_2$, $Fe(NO_3)_3$, $CdCO_3$, $CdSO_4$, $FeSO_4$, $ZnSO_4$, $Fe_2O_3$, CdO, $Ga_2O_3$, $Ln_2O_3$, ZnO, SnO, $SnO_2$, $Fe(OH)_3$, $Zn(OH)_2$, FeOOH, FeO(OH), $Cd(CH_3COO)_2$, Iron perchlorate, Copper perchlorate, Copper EDTA complex, Nickel alkylamine complex, Iron piperidine complex, Cadmium pyridine complex, Iron bipyridine salt and Iron acac complex, wherein the 2D material is selected from the group consisting of graphene, porous graphene, graphene nanoparticles, single walled CNT, and TiC, wherein the electron facilitator is selected from the group consisting of neutral red, azo-dyes, iron porphyrin complex, Schiff base complex, multi walled CNT, Cd (II) or Cu (II) imidazole complex, and Ruthenium complex, and wherein the surfactant is selected from the group consisting of sodium lauryl sulfate, Lauryl dimethyl amine oxide, Cetyltrimethylammonium bromide, Polyethoxylated alcohol, Polyoxyethylene sorbitan Octoxynol, N, N-dimethyldodecylamine-N-oxide, Hexadecyltrimethylammonium bromide, Polyoxyl 10 lauryl ether, sodium deoxycholate, sodium cholate, Polyoxyl castor oil, Nonylphenol ethoxylate, Cyclodextrins, Lecithin, and Methylbenzethonium chloride;

adding the semiconducting hybrid solution to the electroactive microorganism culture to obtain an initiator culture;

providing a counter ion precursor to the initiator culture to form a semi-conducting biogenic hybrid catalyst to obtain a mixed culture, wherein the counter ion precursors are organosulfur compounds, wherein the organosulfur compounds are selected from the group consisting of hydrocarbon mercaptans, alcohol containing mercaptans, mercapto amino acids, mercapto peptides, mercaptopyrimidines, mercapto purines, thioethers, disulfides, thiocarboxylic acids, thioesters, sulfonium salts, sulfoxides, sulfones, thioketones, thioamides, thiocyanates, isothiocyanates, thiocarbamates, and dithiocarbamates;

separating the semi-conducting biogenic-hybrid catalyst from the mixed culture;

adding the semi-conducting biogenic hybrid catalyst to a culture medium in a transparent reactor, wherein the semi-conducting biogenic hybrid catalyst consists of the electroactive microorganism, and semi conducting particles, wherein the semi conducting particles consist of a precursor metal component, the electron facilitator, the at least one 2D material, the surfactant, and the counter ion precursor, wherein the semi conducting particles are located on a cell surface of the electroactive microorganism, wherein the precursor metal component is selected from the group consisting of a metal halide, a metal nitrate, a metal perchlorate, a metal carbonate, a metal sulfate, a metal oxide, a metal hydroxide, a metal oxyhydroxide, an iron and copper EDTA complex, metal amines or bipyridine salt complex of iron, zinc and nickel, a metal carboxylate, and a metal acetylacetonate complex of iron, copper, cadmium, and nickel;

sparging the biogas through the culture medium and irradiating the transparent reactor with a light source; and recovering the fuel precursors from the culture medium;

wherein the fuel precursors are selected from the group consisting of methanol, ethanol, acetic acid, butanol, isopropanol, butyric acid, and caproic acid.

7. The method of claim 6, wherein the semiconducting particle comprises graphene nanoparticles, titanium carbide, and divalent cadmium-ion ($Gr-Np+TiC+Cd^{2+}$).

8. The method of claim 6, wherein the method is performed in a batch mode or in a continuous mode.

9. The method of claim 8, wherein the continuous mode is carried out in a plurality of reactors, wherein the plurality of reactors are placed parallel to each other.

10. The method of claim 6, wherein the light source is an intermittent light source.

11. The method of claim 6, wherein the light source is direct sunlight or LED lights.

\* \* \* \* \*